US007009038B2

(12) United States Patent
Depre et al.

(10) Patent No.: US 7,009,038 B2
(45) Date of Patent: Mar. 7, 2006

(54) PDJA1, A CARDIAC SPECIFIC GENE, CORRESPONDING PROTEINS, AND USES THEREOF

(75) Inventors: Christophe Depre, New York, NY (US); Stephen F. Vatner, New York, NY (US)

(73) Assignee: Univ. of Medicine & Dentistry of N.J., New Brunswick, NJ (US)

( * ) Notice: Subject to any disclaimer, the term of this patent is extended or adjusted under 35 U.S.C. 154(b) by 22 days.

(21) Appl. No.: 10/429,223

(22) Filed: May 2, 2003

(65) Prior Publication Data

US 2004/0009513 A1    Jan. 15, 2004

Related U.S. Application Data

(60) Provisional application No. 60/377,578, filed on May 2, 2002.

(51) Int. Cl.
C07K 1/00   (2006.01)
C07K 14/00  (2006.01)
C07K 17/00  (2006.01)

(52) U.S. Cl. ........................................ 530/350; 514/12
(58) Field of Classification Search ................ 530/350; 514/2; 435/69.1
See application file for complete search history.

(56) References Cited

FOREIGN PATENT DOCUMENTS

WO   WO 01/53312   *   8/2001

OTHER PUBLICATIONS

Hata et al., Murine cDNA enoding a novel type I HSP40/DNAJ homolog, mmDjA4, Biochim. Biophys. Acta (2000), 1493, 1493, p. 208-210.*
Terada et al., Human DnaJ homologs dj2 and dj3, and bag-1 are positive cochaperons of hsc70, J. Biol. Chem., (2000), 275, p. 24728-24734.*
Ohtsuka, Kenzo et al. (2000) "Mammalian HSP40/DNAJ homologs: cloning of novel cDNAs and a proposal for their classification and nomenclature" Cell Stress & Chaperones. vol.: 5, No. 2, pp. 98-112.
Russell, Rick et al. (1999) "DnaJ Dramatically Stimulates ATP Hydrolysis by DnaK: Insight into Targeting of Hsp70 Protein Substrates" Biochemistry. vol.: 38, pp. 4165-4176.
Minami, Yasufumi et al. (1996) "Regulation of the Heat-shock Protein 70 Reaction Cycle by the Mammalian DnaJ Homolog, Hsp40" J. of Biological Chem. vol.: 271, No. 32, pp. 19617-19624.
Depre, Christophe et al. (2001) "Gene program for cardiac cell survival induced by transient ischemia in conscious pigs" Proc Natl Acad Sci USA vol.: 98 No. 16, pp. 9336-9341.
Shu, Won-Chul et al. (1998) "Interaction of the Hsp70 molecular chaperone, DnaK, with its cochaperone DnaJ" Proc Natl Acad Sci USA vol.: 95, pp. 15223-15228.
Diefenbach, Jorg et al. (2000) "The membrane-bound DnaJ protein located at athe cytosolic site of glyoxysomes specifically binds the cytosolic isoform 1 of Hsp70 but not other Hsp70 species" Eur J. Biochem vol.: 267, pp. 746-754.
Laufen, Thomas et al. (1999) "Mechanism of regulation of Hsp70 chaperones by DnaJ cocaperones" Proc Natl Acad Sci USA vol.: 96, pp. 5452-5457.
Hunter, Patricia J. et al (1999) "Mrj encodes a DnaJ-related co-chaperone that is essential for murine placental development" Development vol.: 126, pp. 1247-1258.
Kobayashi, Yasushi et al. (2000) "Chaperones Hsp70 and Hsp40 Suppress Aggregate Formation and Apoptosis in Cultured Neuronal Cells Expressing Truncated Androgen Receptor Protein with Expanded Polyglutamine Tract" J of Biological Chemistry vol.: 275, No. 12 pp. 8772-8778.
Greene, Michael K. et al. (1998) "Role of the J-domain in the cooperation of Hsp40 with Hsp70" Proc Natl Acad Sci USA vol.: 95, pp. 6108-6113.

* cited by examiner

*Primary Examiner*—Robert A. Wax
*Assistant Examiner*—Agnes Rooke
(74) *Attorney, Agent, or Firm*—Klauber & Jackson

(57) ABSTRACT

The present invention provides novel nucleic acid and protein sequences for methods and compositions for treating, screening, and diagnosing cardiovascular disease and methods for using these genes and gene products for prevention of cardiac cell death and prevention of cardiac tissue damage resulting from ischemic events in cardiac tissue, as well as other tissue that is subject to damage resulting from an ischemic event. The genes, gene products and agents of the invention are also useful for treating other related clinical or coronary events such as angina, myocardial infarct (MI), and stroke, for monitoring the effectiveness of their treatment, and for drug development. The genes, gene products and agents of the present invention are also provided as pharmaceutical compositions for treatment of cardiovascular disease, ischemic heart disease, myocardial infarct and related conditions. Kits are also provided for the diagnosis, treatment and prognosis of cardiac diseases and related conditions.

7 Claims, 8 Drawing Sheets

FIG. 1A

AGACGCTGCGTTTGCNGGCTTTGATGAAAGAGTGCGGCGTGCCGGCGGAGAGACAAG ATG GTG AAG GAG ACC CAG TAC TAT GAC ATC
                                                         M   V   K   E   T   Q   Y   Y   D   I

CTG GGG GTG AAG CCC AGC GCC TCC CCG GAG GAG ATC AAG AAG GCC TAT CGG AAG CTG GCG CTG AAG TAC CAC CCG
 L   G   V   K   P   S   A   S   P   E   E   I   K   K   A   Y   R   K   L   A   L   K   Y   H   P

GAC AAG AAC CCG GAT GAG GGC GAG AAG TTT AAG CTC ATA TCC CAG GCA TAT GAA GTA CTT TCA GAT CCA AAG AAA
 D   K   N   P   D   E   G   E   K   F   K   L   I   S   Q   A   Y   E   V   L   S   D   P   K   K

AGG GAC ATT TAT GAC CAG GGT GGC GAG ATG GCG ATT AAG GAA GGA GCT AGA CGG AGC CCC AGC TTC TCT CCC
 R   D   I   Y   D   Q   G   G   E   Q   A   I   K   E   G   A   R   R   S   P   S   F   S   P

ATG GAC ATC TTC GAC ATG TTC TTT GGT GGC GGA GGA CGG AGA GAG AGG CGG AAG AAT GTT GTA CAT
 M   D   I   F   D   M   F   F   G   G   G   G   R   R   E   R   R   G   K   N   V   V   H

CAG TTG TCT GTA ACT CTT GAA GAT TTA TAT AAT GGA GTC ACA AAG AAA TTG GCT CTC CAG AAA GTA ATT TGT
 Q   L   S   V   T   L   E   D   L   Y   N   G   V   T   K   K   L   A   L   Q   K   N   V   I   C

GAG AAA TGT GAA GGC GTT GGC GGG AAG GGA TCT GTG GAG AAG TGC CCC GTG TGC CGA GGG ATG CAG
 E   K   C   E   G   V   G   G   K   G   S   V   E   K   C   P   V   C   R   G   M   Q

ATT CAC CAG CAG ATA GGG CAG GTG ATG GTG CAG CAG ATC GTG TGC ATC GAG TGC AAG GGC GGC
 I   H   Q   Q   I   G   Q   V   M   V   Q   Q   I   V   C   I   E   C   K   G   G

GAG CGC ATC AAC CCC AAG GAC CGC TGC AAA AAC TGC GAA GTC CGG GAG AAG AAG ATC ATT GAG
 E   R   I   N   P   K   D   R   C   K   N   C   E   V   R   E   K   K   I   I   E

GTG CAC GTG GAG AAA GGT ATG ATG AAA GAT GGG CAA AAG ATA CTG TTT CAT CAT GGA GAT CAG AAG CCT GAG CTG
 V   H   V   E   K   G   M   M   K   D   G   Q   K   I   L   F   H   H   G   D   Q   K   P   E   L

GAG CCT GGT GAT GTC ATA ATT GTG CTT GAT CAG AAG CAT CAT CCT GTA TTT CAG AGA CGA GGC CAT GAC TTG ATC
 E   P   G   D   V   I   I   V   L   D   Q   K   H   H   P   V   F   Q   R   R   G   H   D   L   I

FIG. 1B

```
ATG AAA ATG AAA ATT CAG CTT TGT GAA GCC CTG TGT GGC TTC AAG AAG ACG ATA AAA ACA CTG GAT GAT CGA GTC
 M   K   M   K   I   Q   L   C   E   A   L   C   G   F   K   K   T   I   K   T   L   D   D   R   V
CTT GTT ATT ACA TCC AAA TCA GGT GAG GTG ATA AAG CAC GGG GAC CTG AAA TGT GTG CGT AAT GAA GGA ATG CCC
 L   V   I   T   S   K   S   G   E   V   I   K   H   G   D   L   K   C   V   R   N   E   G   M   P
ATC TAC AAA GCA CCC CTG GAG AAA GGG ACT CTG ATC CAG TTT TTA GTT ATT TTT CCT GAA AAA CAC TGG CTT
 I   Y   K   A   P   L   E   K   G   T   L   I   Q   F   L   V   I   F   P   E   K   H   W   L
CCT CAA GAC AAG CTT CCC CAG CTG CTC CCT CGA CAG AAA GTC CAG CAC AGG GAG GCC TAC GAG GAC ATG GAT
 P   Q   D   K   L   P   Q   L   L   P   R   Q   K   V   Q   H   R   E   A   Y   E   D   M   D
CAG GTG GAG CTG AAG GAG TTT AAT CCC AAT GAG CAG AAC TGG CGC CAG CAC CAG GAG GAG GAC GAT
 Q   V   E   L   K   E   F   N   P   N   E   Q   N   W   R   Q   H   Q   E   E   D   D
GAC GGG CCC CGG GCC GGC GTG CAG ACG GCA TGA GGGGGCCCCGGAGCAGCATGGCCCAGCTGGACTAGCACTGACTGAATG
 D   G   P   R   A   G   V   Q   T   A   *
TAAAGTTGGCACAATGAAAATGGCATGCGCTTTAAATGGCCTCGTTCCCTGTGTATGTGTTCAGCATTCTCAACTGCTGAGTGTCTTTTGG
TTTTTCTTTGTTTTCTTTTGGTTGTAACTTAAGTTATAGCTTAATTTATATTTTAAATGTTTAAGTGTAAATCACTTCTAGTCTGCATATGAATCT
GTTCATTTACATTTTCAGGAGAAACTTCTGAGATACCAGTGACCGCACTGACACTTTGTGCTTTCAGTGGCTTTGCCATAATTCATTTCTACCATAAAGC
ACAGCCCAGTGAACAGCACTTAGCTCCCCTAGCAAACTGGCTCATCTCTTGCCTCTCTTGCCTCCCCTGC
CCCCCATGGCAAAATTATGAGGGTATGATCTCAGGGCTGCTAATGTGGCATTTCCAAATCTAGATGATTCTCCTCAAGAATAAAAGCACATCTGTGAT
TGGACTTGGCTGCAGGGCCAACTTGGTTCCTCCTCGTTCGTGCCCGTGAATGTTTGAGTGTGTCGATCATCTCTTGGAAGCTTC
CTGAACCTTCCAAGCCTTGTGGTGAGGACAAAACCAGTGTTTAAATGAAAGCGCTGATAAAACGAAACCATCCGTGTCCCCAGCAGCCTCAGTGCAGCAACAGA
CTTCTGTTGACAGCCTTTGCAGTGCTCTCCCACCAAGTGCTTACTTGTAAAGAAAACGAAACCATCCGTGTCCCCAGCAGCCTCAGTGCAGCAACAGA
```

FIG. 1C

AGCCTTGGGAGAATGCTGGTGTTCGGCCCATGGCACAGCCAGCTTCCCTGTCTGACCACTGATCCTGACTGAGGGTCTGGAAAGGCAGAGAA
CATCTCAGTGTTCCCACCTCATTCTCCCAGATTCAACTCCCCTTCCAAAGGATGGTTCCTTCCTTGCACAGCCATATCACAAAGGGCTTCCTGCTCAA
GGGATAAATGTTTTAATTTTAGTGAGAACTAAAGCTCTACTCTGGACTGCAGTCTCTATAGACTGCCATGTAAATGATAGCTTGTTTGAAGGGACACGAGTC
ATTAATTTTCTGGCAGTAGACTACAGTTTAAATTTAGGGCTACCTCAACCTTTAGCCACTACTCCTTTCCTTCCCGCAATACTCACAAAGAAAAATTG
CTGCCTTTCTAAGCTGCTGGGTTAAAGCAGAGAGGCCACTTTTCAGATACACACCCTTACTTGGTTATACAGTACTGAGAGTTTGACTGAGGCCAGGGACCT
CCCCAGGAGGGCCAAAGGCAGATCAGACCCATGGCAGGTAGGTCCAGAGGATGACCAGTCTCCAGCAGAAGATTGCTGACTAGTGGGTGGGCACAAT
TTGCGCAAATAAGGTATAAAAAGCTACCTGTCCCACTTTGACCAATAGTCAGGAAGACATAAAACCTATTCTTTCAAATAAGCCTATATGAAAATC
AATTTACAAATGGACCACAACTCCAGGGTGTTTGTTTCTGTGCTGTGACTTCCTAATAAATTACTGCTAGAAAATTACTGTCTAGTTGATGATGGGGC
AAAATTACATTCAGTCCTTGTCATGTAATAGAATTTGGAGGGTGTGCTTGAAATTTATGCCACCTGTACATTTGTCAGCTTAAATTAAAATCAAGC
TGGTATGAGAGACAAAAAAAAAAAAAAAA

FIG. 2

[Sequence alignment between hHSP40 and pDJA1 — figure content]

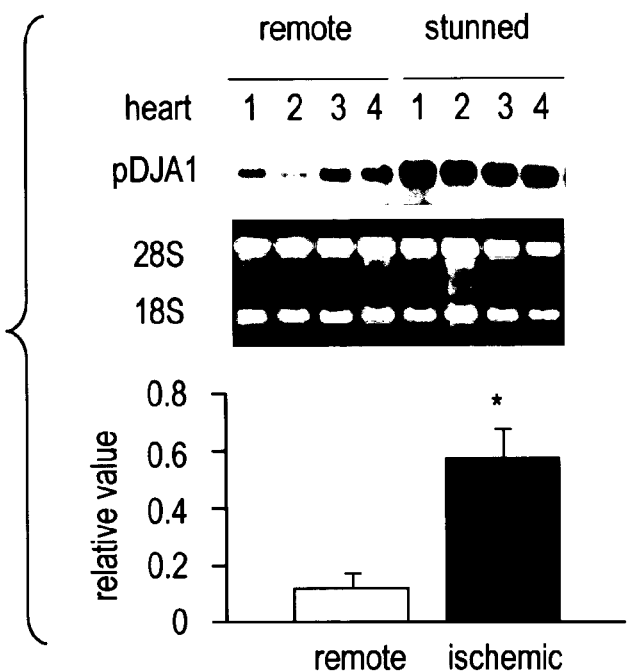
FIG. 5A
FIG. 5B
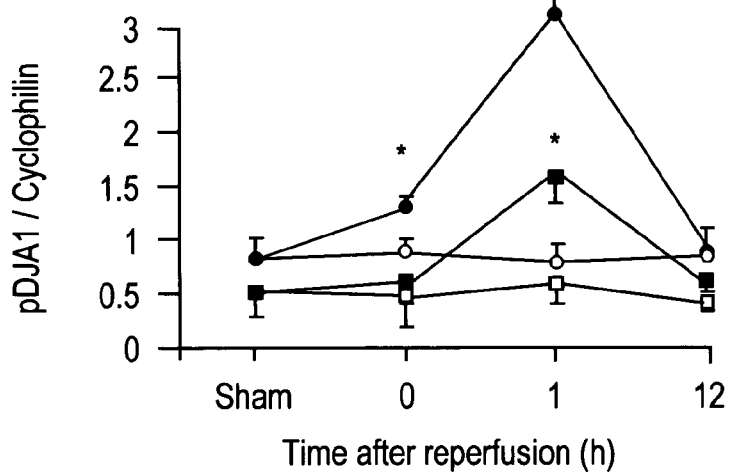
FIG. 5C
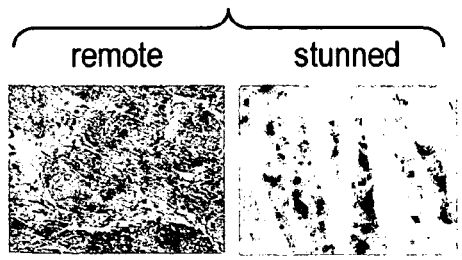

SEQUENCE LISTING

```
<160> NUMBER OF SEQ ID NOS: 7

<210> SEQ ID NO 1
<211> LENGTH: 3014
<212> TYPE: DNA
<213> ORGANISM: Sus scrofa
<220> FEATURE:
<221> NAME/KEY: misc_feature
<222> LOCATION: 16
<223> OTHER INFORMATION: n = A,T,C or G

<400> SEQUENCE: 1
agacgctgcg tttgcnggct ttgatgaaag agtgcggcgg tgccgggcgc ggagagacaa      60
gatggtgaag gagacccagt actatgacat cctgggggtg aagcccagcg cctccccgga     120
```

-continued

```
ggagatcaag aaggcctatc ggaagctggc gctgaagtac cacccggaca agaacccgga    180
tgagggcgag aagtttaagc tcatatccca ggcatatgaa gtactttcag atccaaagaa    240
aagggacatt tatgaccagg gtggcgagca ggcgattaag gaaggaggct caggcagccc    300
cagcttctct tcccccatgg acatcttcga catgttcttt ggtggcggag acggatggc    360 tagagagaga agaggcaaga atgttgtaca tcagttgtct gtaactcttg aagatttata    420
taatggagtc acaaagaaat tggctctcca gaaaaatgta atttgtgaga atgtgaagg    480 cgttggcggg aagaagggat ctgtggagaa gtgccccgtg tgcaaggggc gagggatgca    540
gattcacatc cagcagatag ggccaggcat ggtgcagcag atccagactg tgtgcatcga    600
gtgcaagggc cagggcgagc gcatcaaccc caaggaccgc tgcgaaaact gcagtggtgc    660
caaggtcatc cgggagaaga agatcattga ggtgcacgtg gagaaaggta tgaaagatgg    720
gcaaaagata ctgtttcatg gagaaggaga tcaggagcct gagctggagc ctggtgatgt    780
cataattgtg cttgatcaga aggatcatag tgtctttcag agacgaggcc atgacttgat    840
catgaaaatg aaaattcagc tttgtgaagc cctgtgtggc ttcaagaaga cgataaaaac    900
actggatgat cgagtccttg ttattacatc caaatcaggt gaggtgataa agcacgggga    960
cctgaaatgt gtgcgtaatg aaggaatgcc catctacaaa gcaccctgg agaaagggac    1020 tctgatcata cagttttag ttattttcc tgaaaaacac tggcttcctc aagacaagct    1080
tccccagctg gaagctctgc tccctcctcg acagaaagtc aggataacgg acgacatgga    1140
tcaggtggag ctgaaggagt ttaatcccaa tgagcagaac tggcgccagc acagggaggc    1200
ctacgaggag gacgatgacg ggccccgggc cggcgtgcag tgccagacgg catgagggg    1260 ccccggagca gcatggccca gctggactag cactgatgaa tgtaaagttg cacaatgaa    1320 aatggcatcg cttttaatggc ctcgtgtttg gggtgtcctg tgtatgtgtt cagcattctc    1380
aactgctgag tgtctttttg gttttttcttt tgttttttctt ttggttgtaa cttaagttat    1440
agcttaattt atatttaaat gttttaagtg taaatcactt ctagtctgca tatggaatct    1500
gttcatttac attttcagga aacttctgag ataccagtga ccgcactgac actttgtgct    1560
tctagtggct ttgccataat tcatttctac caataaagca cagcccagtg aacagcactt    1620
agctccctag caaacctcca ggcatgaagt gggcgaactg gctcatctct tgctccgtgc    1680
ctctttgcct ccccctgccc cccatggcaa aattatgagg gtatgatctc agggctgcta    1740
atgtggcatt tccaaatcta gatgattctc ctcaagaata aaagcacatc tgtggattgg    1800
acttggctgc agggccaact tggttcctcc tgttctgtgc ccgtgaatgt ttggaatagg    1860
gtgtgagtgt gtctgatcat ctctcttgga agcttcctga accttccaag ccttgtggtg    1920
aggacaaacc agtgttttaa atgaaacgct gataaaactg tttgtgtgcg acccctgcac    1980
tgttgtgtgt tttatcttct gttgacagcc tttgcagtgc tctcccacca aagtgcttac    2040
ttgtaaagaa aacgaaacca tccgtgtccc cagcagcctc agtgcagcaa cagaagcctt    2100
gggagaatgc tggtggttcg gccccatggc acagccagct tccctgtctg accactgatc    2160
ctggatgact tgagggtctg gaaaggcaga gaacatctca gtgtttccca cctcattctc    2220
ccagattcaa ctcccttcca aaggatggtt ccttttcttg cacagccata tcacaaaggg    2280
cttcctgctc aagggataat gttttatta gtgagaacta aagctctact ctggactgca    2340
gtctctatag actgccatgt aaatgatagc ttgtttgaag ggacacgagt cattaatttt    2400
ctggcaggta gactacagtt taaatttagg gctacctcaa cctttagcca ctactccttt    2460
```

```
ccttcccgca atactcacaa agaaaaattg ctgcctttct aagctgctgg gttaaagcag    2520
aggccacttt tcagatacac ccttacttgg ttatacagta cctgagagtt tgactgaggc    2580
cagggacctc cccaggaggg ccaaagggca gatcagaccc atggcaggta ggtccagagg    2640
atggaccagt ctccagcaga agattgctga ctagtgggtg ggcacaattt gcgcaaataa    2700
ggtataaaaa agcctacctg tcccactttg accaatagtc aggaaagaca taaaacctat    2760
tctttcaaat aagcctatat gaaatcaat ttacaaatgg accacaactc cagggtgttt    2820
tgtttctgtg ctgtgacttc ctaataaatt actgctagaa aattactgtc tagttgatga    2880
tggggcaaaa ttacattcag ctccttgtca tgtaatagaa tttggagggt gttgcttgaa    2940
atttatgcca cctgtacatt tgtcagctta aaattaaaat caagctggta tgagagacaa    3000
aaaaaaaaaa aaaa                                                      3014
```

<210> SEQ ID NO 2
<211> LENGTH: 397
<212> TYPE: PRT
<213> ORGANISM: Sus scrofa

<400> SEQUENCE: 2

```
Met Val Lys Glu Thr Gln Tyr Tyr Asp Ile Leu Gly Val Lys Pro Ser
  1               5                  10                  15

Ala Ser Pro Glu Glu Ile Lys Lys Ala Tyr Arg Lys Leu Ala Leu Lys
             20                  25                  30

Tyr His Pro Asp Lys Asn Pro Asp Glu Gly Glu Lys Phe Lys Leu Ile
         35                  40                  45

Ser Gln Ala Tyr Glu Val Leu Ser Asp Pro Lys Lys Arg Asp Ile Tyr
     50                  55                  60

Asp Gln Gly Gly Glu Gln Ala Ile Lys Glu Gly Ser Gly Ser Pro
 65                  70                  75                  80

Ser Phe Ser Ser Pro Met Asp Ile Phe Asp Met Phe Phe Gly Gly Gly
                 85                  90                  95

Gly Arg Met Ala Arg Glu Arg Arg Gly Lys Asn Val Val His Gln Leu
            100                 105                 110

Ser Val Thr Leu Glu Asp Leu Tyr Asn Gly Val Thr Lys Lys Leu Ala
        115                 120                 125

Leu Gln Lys Asn Val Ile Cys Glu Lys Cys Glu Gly Val Gly Gly Lys
    130                 135                 140

Lys Gly Ser Val Glu Lys Cys Pro Val Cys Lys Gly Arg Gly Met Gln
145                 150                 155                 160

Ile His Ile Gln Gln Ile Gly Pro Gly Met Val Gln Gln Ile Gln Thr
                165                 170                 175

Val Cys Ile Glu Cys Lys Gly Gln Gly Glu Arg Ile Asn Pro Lys Asp
            180                 185                 190

Arg Cys Glu Asn Cys Ser Gly Ala Lys Val Ile Arg Glu Lys Lys Ile
        195                 200                 205

Ile Glu Val His Val Glu Lys Gly Met Lys Asp Gly Gln Lys Ile Leu
    210                 215                 220

Phe His Gly Glu Gly Asp Gln Glu Pro Glu Leu Glu Pro Gly Asp Val
225                 230                 235                 240

Ile Ile Val Leu Asp Gln Lys Asp His Ser Val Phe Gln Arg Arg Gly
                245                 250                 255

His Asp Leu Ile Met Lys Met Lys Ile Gln Leu Cys Glu Ala Leu Cys
            260                 265                 270
```

-continued

```
Gly Phe Lys Lys Thr Ile Lys Thr Leu Asp Asp Arg Val Leu Val Ile
            275                 280                 285

Thr Ser Lys Ser Gly Glu Val Ile Lys His Gly Asp Leu Lys Cys Val
290                 295                 300

Arg Asn Glu Gly Met Pro Ile Tyr Lys Ala Pro Leu Glu Lys Gly Thr
305                 310                 315                 320

Leu Ile Ile Gln Phe Leu Val Ile Phe Pro Glu Lys His Trp Leu Pro
                325                 330                 335

Gln Asp Lys Leu Pro Gln Leu Glu Ala Leu Leu Pro Pro Arg Gln Lys
            340                 345                 350

Val Arg Ile Thr Asp Asp Met Asp Gln Val Glu Leu Lys Glu Phe Asn
        355                 360                 365

Pro Asn Glu Gln Asn Trp Arg Gln His Arg Glu Ala Tyr Glu Glu Asp
370                 375                 380

Asp Asp Gly Pro Arg Ala Gly Val Gln Cys Gln Thr Ala
385                 390                 395

<210> SEQ ID NO 3
<211> LENGTH: 334
<212> TYPE: PRT
<213> ORGANISM: Homo sapiens

<400> SEQUENCE: 3

Met Gly Lys Asp Tyr Tyr Cys Ile Leu Gly Ile Glu Lys Gly Ala Ser
1               5                   10                  15

Asp Glu Asp Ile Lys Lys Ala Tyr Arg Lys Gln Ala Leu Lys Phe His
            20                  25                  30

Pro Asp Lys Asn Pro Gln Ala Glu Glu Lys Phe Lys Glu Val Ala Glu
        35                  40                  45

Ala Tyr Glu Val Leu Ser Asp Pro Lys Lys Arg Glu Ile Tyr Asp Gln
    50                  55                  60

Phe Gly Glu Glu Gly Leu Lys Gly Gly Ala Gly Gly Asp Gly Gln Gly
65                  70                  75                  80

Gly Thr Phe Arg Tyr Thr Phe His Gly Asp Pro His Ala Thr Phe Ala
                85                  90                  95

Ala Phe Phe Gly Gly Glu Asn Pro Phe Glu Ile Phe Phe Gly Arg Arg
            100                 105                 110

Met Gly Gly Gly Arg Asp Ser Glu Glu Met Glu Ile Asp Gly Asp Pro
        115                 120                 125

Phe Ser Ala Phe Gly Phe Ser Met Asn Gly Tyr Pro Arg Asp Arg Asn
    130                 135                 140

Ser Val Gly Pro Ser Arg Leu Lys Gln Asp Pro Pro Val Ile His Glu
145                 150                 155                 160

Leu Arg Val Ser Leu Glu Glu Ile Tyr Ser Gly Cys Thr Lys Arg Met
                165                 170                 175

Lys Ile Ser Arg Lys Arg Leu Asn Ala Asp Gly Arg Ser Tyr Arg Ser
            180                 185                 190

Glu Asp Lys Ile Leu Thr Ile Glu Ile Lys Lys Gly Trp Lys Glu Gly
        195                 200                 205

Thr Lys Ile Thr Phe Pro Arg Glu Gly Asp Glu Thr Pro Asn Ser Ile
    210                 215                 220

Pro Ala Asp Ile Val Pro Ile Ile Lys Asp Lys His Pro Lys Arg
225                 230                 235                 240

Lys Arg Asp Gly Ser Asn Ile Ile Tyr Thr Ala Lys Ile Ser Leu Arg
                245                 250                 255
```

-continued

Glu Ala Leu Cys Gly Cys Ser Ile Asn Val Pro Thr Leu Asp Gly Arg
                260                 265                 270

Asn Ile Pro Met Ser Val Asn Asp Ile Val Lys Pro Gly Met Arg Arg
            275                 280                 285

Arg Ile Ile Gly Tyr Gly Leu Pro Phe Pro Lys Asn Pro Asp Gln Lys
        290                 295                 300

Gly Asp Leu Leu Ile Glu Phe Glu Val Ser Phe Pro Asp Thr Ile Ser
305                 310                 315                 320

Ser Ser Ser Lys Glu Val Leu Arg Lys His Leu Pro Ala Ser
                325                 330

<210> SEQ ID NO 4
<211> LENGTH: 397
<212> TYPE: PRT
<213> ORGANISM: Sus scrofa

<400> SEQUENCE: 4

Met Val Lys Glu Thr Gln Tyr Tyr Asp Ile Leu Gly Val Lys Pro Ser
  1               5                  10                  15

Ala Ser Pro Glu Glu Ile Lys Lys Ala Tyr Arg Lys Leu Ala Leu Lys
                 20                  25                  30

Tyr His Pro Asp Lys Asn Pro Asp Glu Gly Glu Lys Phe Lys Leu Ile
             35                  40                  45

Ser Gln Ala Tyr Glu Val Leu Ser Asp Pro Lys Lys Arg Asp Ile Tyr
         50                  55                  60

Asp Gln Gly Gly Glu Gln Ala Ile Lys Glu Gly Ser Gly Ser Pro
 65                  70                  75                  80

Ser Phe Ser Ser Pro Met Asp Ile Phe Asp Met Phe Gly Gly Gly
                 85                  90                  95

Gly Arg Met Ala Arg Glu Arg Arg Gly Lys Asn Val Val His Gln Leu
                100                 105                 110

Ser Val Thr Leu Glu Asp Leu Tyr Asn Gly Val Thr Lys Lys Leu Ala
            115                 120                 125

Leu Gln Lys Asn Val Ile Cys Glu Lys Cys Glu Gly Val Gly Gly Lys
130                 135                 140

Lys Gly Ser Val Glu Lys Cys Pro Val Cys Lys Gly Arg Gly Met Gln
145                 150                 155                 160

Ile His Ile Gln Gln Ile Gly Pro Gly Met Val Gln Gln Ile Gln Thr
                165                 170                 175

Val Cys Ile Glu Cys Lys Gly Gln Gly Glu Arg Ile Asn Pro Lys Asp
            180                 185                 190

Arg Cys Glu Asn Cys Ser Cys Ala Lys Val Ile Arg Glu Lys Lys Ile
        195                 200                 205

Ile Glu Val His Val Glu Lys Cys Met Lys Asp Gly Gln Lys Ile Leu
    210                 215                 220

Phe His Gly Glu Cys Asp Gln Glu Pro Glu Leu Glu Pro Gly Asp Val
225                 230                 235                 240

Ile Ile Val Leu Asp Gln Lys Asp His Ser Val Phe Gln Arg Arg Gly
                245                 250                 255

His Asp Leu Ile Met Lys Met Lys Ile Gln Leu Cys Glu Ala Leu Cys
            260                 265                 270

Gly Phe Lys Lys Thr Ile Lys Thr Leu Asp Asp Arg Val Leu Val Ile
        275                 280                 285

Thr Ser Lys Ser Gly Glu Val Ile Lys His Gly Asp Leu Lys Cys Val

-continued

```
                    290                 295                 300
Arg Asn Glu Gly Met Pro Ile Tyr Lys Ala Pro Leu Glu Lys Gly Thr
305                 310                 315                 320

Leu Ile Ile Pro Val Leu Val Val Phe Pro Arg Lys His Trp Leu Pro
                325                 330                 335

Gln Asp Lys Leu Pro Gln Leu Glu Ala Leu Leu Pro Pro Arg Gln Lys
                340                 345                 350

Val Arg Ile Thr Asp Asp Met Asp Gln Val Glu Leu Lys Glu Phe Asn
                355                 360                 365

Pro Asn Glu Gln Asn Trp Arg Gln His Arg Glu Ala Tyr Glu Glu Asp
                370                 375                 380

Asp Asp Gly Pro Arg Ala Gly Val Gln Cys Gln Thr Ala
385                 390                 395

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ctctcttgga agcttcctga ac                                      22

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
gcactgcaaa ggctgtcaa                                          19

<210> SEQ ID NO 7
<211> LENGTH: 29
<212> TYPE: DNA
<213> ORGANISM: Artificial Sequence
<220> FEATURE:
<223> OTHER INFORMATION: Probe

<400> SEQUENCE: 7
aagcttgtgg tgaggacaaa ccagtgttt                               29
```

PDJA1, A CARDIAC SPECIFIC GENE, CORRESPONDING PROTEINS, AND USES THEREOF

CROSS-REFERENCE TO RELATED APPLICATIONS

The present application is a non-provisional application claiming the priority of now abandoned provisional U.S. Ser. No. 60/377,578, filed on May 2, 2002, the disclosure of which is hereby incorporated by reference herein in its entirety. Applicants claim the benefits of this application under 35 U.S.C. §119(e).

GOVERNMENT RIGHTS CLAUSE

The research leading to the present invention was supported, at least in part, by National Institutes of Health grants HL33065, PO1 HL 59139, PO1 HL 69020, AG 14121 and HL 33107 and AHA Scientist Development Grant 0230017N. Accordingly, the Government may have certain rights in the invention.

FIELD OF THE INVENTION

The invention relates generally to the field of cardiology and the identification of genes and gene products involved in protection of cardiac tissue against irreversible ischemic damage. More particularly, the present invention relates to methods of identifying and cloning novel cardioprotective genes, expressing the gene products, and methods of using the genes or gene products for prevention or treatment of damage to heart tissue arising from ischemic events. Methods for diagnosing ischemic cardiac events are also envisioned by use of the genes or gene products of the present invention. Methods of using a nucleic acid and/or a protein, expressed in cardiac cells, to treat or prevent heart damage and antibodies against the protein, to diagnose heart damage, are provided for by the present invention. The instant invention also provides compositions comprising, and methods of using products of a novel gene designated pDJA1 and associated variants thereof. Such gene products, as well as their binding partners, agonists, and antibodies to the gene products can be used for the prevention, diagnosis, prognosis and treatment of cardiovascular disease.

BACKGROUND OF THE INVENTION

Cardiovascular disease, including, but not limited to, atheroslerosis, ischemia, reperfusion, hypertension, restenosis and arterial inflammation, is a major health risk throughout the world. Ischemia is a condition wherein there is a lack of oxygen supply in tissues or organs due to inadequate perfusion due to atheroslerosis or restenotic lesions, stroke, or anemia, to name a few. The most common cause of ischemia in the heart is atherosclerotic disease of the coronary arteries. Myocardial ischemia can also occur if myocardial oxygen demands are abnormally increased, due to hypertension or aortic stenosis.

One of the most important therapeutic targets in the treatment of cardiovascular disease has been the protection of ischemic myocardium from necrosis. This has been a major focus for basic and applied research over the past 30 years. More recently, mechanisms of programmed cardiac cell death (apoptosis) have also been studied extensively. Both necrosis and apoptosis result in the irreversible loss of contractile performance. An unexplored corollary to protection from cell death is the enhancement of cell survival.

Heat shock proteins are involved in the folding, degradation and translocation of intracellular proteins (Benjamin I, et al., Stress (heat shock) proteins, (1998), *Circ Res.* 83: 117–132), but they also participate in the protection against apoptosis and in cell growth (Mehlen P. et al, Small stress proteins as novel regulators of apoptosis. Heat shock protein 27 blocks FAS/APO-1 and staurosporine-induced cell death. *J Biol Chem.* (1996); 271: 16510–16517; Beere H., et al, Heat-shock protein 70 inhibits apoptosis by preventing the recruitment of procaspase-9 to the Apaf-1 apoptosome, *Nature Cell Bio.*, (2000); 2: 469–475; Li, C. et al., heat shock protein 70 inhibits apoptosis downstream of cytochrome c release and upstream of caspase-3 activation, *J Biol Chem.*, (2000); 275:25665–26571; Kamradt, M., et al., The small heat-shock protein αB-crystallin negatively regulates cytochrome c- and caspase-8-dependent activation of caspase-3 by inhibiting its autoproteolytic maturation, *J Biol Chem.*, (2001); 276: 16059–16063). They are crucial effectors of the program of cell survival, which protects cells against irreversible damage and accelerates functional recovery after stress (Latchman, D., Heat shock proteins and cardiac protection, *Cardiovasc Res.* (2001); 51: 637–646). Two main forms of heat-shock proteins in *E. Coli*, called DnaK and DnaJ, have been conserved in eukaryotes (Kelley, W., How J domains turn on Hsp70s., *Cur Biol.* (1999); 9: R305–R308). In mammalian cells, the chaperone HSP40 is the homologue of DnaJ. Several isoforms of DnaJ-like/HSP40 homologues have been cloned, that differ by their tissue distribution and their protein interactions. The role of these co-chaperones is to stimulate the ATPase activity of the cognate HSP70 (Russell, R., et al., DnaJ dramatically stimulates ATP hydrolysis by DnaK: insight into targetting of Hsp70 proteins to polypeptide substrate, *Biochemistry*, (1999); 38: 4165–4176; Minami, Y., et al., Regulation of the heat-shock protein 70 reaction cycle by the mammalian DnaJ homolog, Hsp40, *J Biol Chem.*, (1996); 271: 19617–19624) and to modulate its substrate-binding capacity. The heat-shock response is particularly developed in cardiac cells, which are long-lived, post-mitotic cells submitted to high oxidative stress (Williams, R., et al., Protective responses in the ischemic myocardium, *J Clin Invest.*, (2000); 106: 813–818). During ischemia/reperfusion, this response is important to tilt the balance between cell survival and cell death.

Myocardial stunning refers to a form of non-lethal, fully reversible myocardial dysfunction that follows an acute episode of ischemia (Heyndrickx, G R, et al., Regional myocardial functional and electrophysiological alterations after brief coronary artery occlusion in conscious dogs, *J Clin Invest.* (1975) 56: 978–985; Kloner, R A., et al., Consequences of Brief Ischemia: Stunning, Preconditioning, and Their Clinical Implications: Part 1, *Circulation*, (2001); 104: 2981–2989). The syndrome of stunning is prevalent in different etiologies of coronary artery disease, including stable or unstable angina pectoris, myocardial infarction, and post-surgical dysfunction (Bolli, R., et al., Molecular and cellular mechanisms of myocardial stunning, *Physiol Rev.*, (1999); 79: 609–634). Due to the major prevalence of ischemic heart disease, stunning is of paramount importance because it corresponds to a condition in which myocardial viability is maintained. Unraveling the molecular mechanisms of cardioprotection in stunned myocardium can open new avenues to salvage dysfunctional cardiac tissue and prevent cardiac cell loss. Especially, a better understanding of the mechanisms by which the molecular and cellular adaptations maintain cell survival should open new therapeutic opportunities.

It would, therefore, be beneficial to provide for specific genes, gene products, compositions and methods for the treatment and diagnosis of cardiac disease, including ischemic cardiac events, and to provide methods that would identify individuals with a predisposition for such conditions, and other types of cardiovascular disease or related conditions, and hence are appropriate subjects for preventive therapy.

SUMMARY OF THE INVENTION

It is well recognized that myocardial ischemia leads to cell death, whether by necrosis or apoptosis, and that survival of postichemic myocardium depends on factors that limit necrosis and/or apoptosis. The present invention relates to the discovery that ischemia, followed by reperfusion induces a gene program of cell survival in cardiac tissue or other tissue exposed to an ischemic event.

A first aspect of the invention provides for the identification, expression and use of genes and gene products that counteract apoptosis, thus acting as cytoprotectants and inducers of cell growth. In a preferred embodiment, a novel gene, designated pDJA1, the nucleic acid sequence of which is provided in SEQ ID NO: 1, and variants thereof, have an expression pattern that is up-regulated in cardiac tissue and cardiac cell lines. The invention relates to the use of said gene, gene products, and agonists of said gene or gene products (pDJA1 and variants thereof, cDNA, RNA, and/or protein, small synthetic organic molecules, antibodies) as targets for diagnosis, drug screening and development of therapies for cardiovascular disease. In a preferred embodiment, the invention provides for methods of using the protein encoded by said gene, provided herein as SEQ ID NO: 2, and variants thereof, or nucleic acids that encode said proteins or variants thereof for the treatment, prevention and diagnosis of cardiovascular disease.

A second aspect of the invention provides for a biomarker associated with and/or predictive of cardiovascular disease including atherosclerosis, coronary heart disease and clinical and coronary events including myocardial infarction, angina, stroke and other related conditions related to or resulting from an ischemic event (eg., an episode wherein tissue such as cardiac tissue is deprived of oxygen for a period of time due to an occlusion, which results in cell death or damage), followed by reperfusion. In a preferred embodiment, the biomarker comprises the nucleic acid of SEQ ID NO: 1. In yet another preferred embodiment, the biomarker comprises the amino acid sequence of SEQ ID NO: 2. The genes encoding this protein biomarker were identified using subtractive hybridization of cardiac tissue in a swine model of transient ischemia. This biomarker correlates with the areas of cardiac tissue that exhibit recovery following the ischemic event and reperfusion thereafter. It is envisioned that the preferred biomarkers, including the nucleic acid of SEQ ID NO: 1 and the polypeptide encoded by the pDJA1 gene identified in SEQ ID NO: 2, may be of diagnostic or prognostic use in a clinical setting. Assays detecting this gene, or variants thereof, the protein or polypeptide or fragments or variants thereof, may be used to assess overall recovery from the ischemic event or to monitor disease progression, and response to therapy. Such assays will augment existing diagnostic methodologies and allow identification and monitoring of patients. They will also facilitate the development of therapeutic agents directed at cardiovascular disease or related conditions, while potentially highlighting new targets for such intervention. In addition, these biomarkers may have predictive value in other chronic/acute disease states in which contributing factors or resulting events in common with cardiovascular disease or atherosclerosis occur including for instance, but not limited to stroke, Alzheimer's Disease, tissue repair and various inflammatory conditions.

A third aspect of the invention provides methods and compositions for treatment of cardiovascular and/or ischemic heart disease, coronary artery disease and clinically related conditions, and for screening and development of agents for treatment of such conditions. Preferred embodiments include use of the genes or gene products of the present invention (eg. SEQ ID NOS: 1 and 2) for delivery to a mammal in need of such therapy. In a further preferred embodiment, the mammal is a human subject.

A fourth aspect of the invention provides methods for diagnosing cardiovascular and/or ischemic heart disease, myocardial infarct, coronary artery disease and clinically related conditions. One embodiment includes the use of the genes or gene products identified by the methods described herein, including but not limited to those genes and gene products identified through use of subtractive hybridization assays in a large mammalian model of cardiac ischemia/reperfusion. In a preferred embodiment, the gene useful for diagnosis of a coronary artery disease, ischemic heart disease, myocardial infarct, carotid artery disease and other clinically related conditions includes the gene identified in the nucleic acid of SEQ ID NO: 1. Another preferred embodiment includes the use of the gene products identified by the methods described herein, including but not limited to the gene product identified as the protein of SEQ ID NO: 2.

A fifth aspect of the invention provides antibodies, e.g., monoclonal and polyclonal and chimeric and bispecific antibodies, capable of immunospecific binding to a specific gene or gene product or any portion or fragment thereof, particularly a gene or gene product disclosed herein. These antibodies may be utilized for diagnostic or therapeutic purposes.

A sixth aspect of the present invention provides pharmaceutical compositions comprising a therapeutically effective amount of the genes or gene products of the present invention, including but not limited to the nucleic acid of SEQ ID NO: 1 or the protein of SEQ ID NO: 2, with a pharmaceutically acceptable carrier for delivery to an individual in need of such therapy. Included in this aspect of the invention are agonists of the gene or gene products identified herein. Such agonists may be small synthetic organic molecules, proteins, peptides, polypeptides or antibodies. A further embodiment comprises a therapeutically effective amount of an agent that upregulates the expression and/or activity of the pDJA1 gene or gene product and a pharmaceutically acceptable carrier. The pharmaceutical compositions may be delivered orally, intravenously, intramuscularly, subcutaneously. intrathecally, intracranially. They may be in the form of tablets, capsules, suspensions, suppositories or in liquid form suitable for intravenous delivery.

A seventh aspect of the invention provides kits that may be used in the above recited methods and that may comprise single or multiple preparations, or antibodies, together with other reagents, e.g., labels, substrates, if needed, and directions for use. The kits may be used for diagnosis of disease, or may be assays for the identification of new diagnostic and/or therapeutic agents, or to identify new targets for therapeutic agents.

An eighth aspect of the invention provides methods of screening for agents that upregulate the expression or the activity, of the genes or gene products of the present invention.

A ninth aspect of the invention provides methods of treating cardiovascular disease, including, but not limited to, coronary heart disease, ischemic heart disease, stroke, atherosclerosis and related conditions, comprising administering to a subject a therapeutically effective amount of an agent or drug that upregulates the expression or activity of genes and gene products that aid in prevention of cardiac cell death. An agent described herein may be used alone or in conjunction with other therapeutic regimens or drugs currently used in the treatment of patients having such cardiac diseases or related conditions. Included in this is the use of the agents of the present invention with standard therapies such as angioplasty or concurrently with the use of stents.

A tenth aspect of the present invention provides for elicitation of a genomic profile promoting cell survival following a myocardial ischemic event, which includes the up-regulation of genes involved in prevention of apoptosis, in cytoprotection and in promotion of cell growth. Furthermore, if a program of cell survival can be stimulated in the ischemic heart, this represents a novel and important therapeutic strategy for patients suffering from or prone to developing cardiovascular disease, or prone to further subsequent ischemic events.

An eleventh aspect of the invention provides for screening and identification of genes that are upregulated by ischemia/reperfusion. In one embodiment, screening is conducted in a large mammalian model of myocardial stunning using cDNA subtractive hybridization (Depre, C., et al., Gene program for cardiac cell survival induced by transient ischemia in conscious pig, *Proc Nat'l Acad Sci. U.S.A.*, (2001); 98: 9336–9341). In particular, the genomic profile of ischemic myocardium was examined in a model that is most relevant to clinical conditions, i.e., a swine model of transient ischemia. Although the majority of investigations on myocardial ischemia are conducted in rodent models, major differences exist between rodents and larger mammals (differences in heart rate, action potential, and calcium handling) (Benjamin I., Circ. Res., (1998), 83:117–132; Mehlen, P. et al. J. Biol. Chem. (1996), 271: 16510–16517). Thus, the best experimental model to elicit a program of cell survival should include a transient episode of ischemia reperfusion without irreversible damage. This model induces myocardial stunning, which may be one of the most frequently encountered sequelae of ischemia in patients with ischemic heart disease (Beere, H. et al. Nature Cell Biol. (2000) 2:469–475). Stunning is the prolonged dysfunction of the ischemic heart that persists after reperfusion despite the normalization of blood flow and that eventually resolves with complete contractile recovery, provided no other ischemic episode intervenes (Li, C. et al. J. Biol. Chem. (2000) 275: 25665–25671); Kamradt, M. et al. J. Biol. Chem. (2001), 276: 16059–16063). The activation of a program of cell survival would explain both the full reversibility of dysfunction in stunned myocardium and the protection against further ischemia, referred to as preconditioning (Latchman et al., Cardiovacs. Res. (2001), 51: 637–646; Kelley W. et al. Curr. Biol. (1999), 9:R305–R308). The genomic response observed parallels the time course of myocardial stunning and differs transmurally, related to the transmural differences in reduction of blood flow during ischemia. One embodiment provides for the identification of genes not previously characterized in myocardium, wherein said genes are identified in a model of transient ischemia followed by prolonged stunning, which elicits a genomic profile of cell survival. The genes that are upregulated in ischemic myocardium encode transcripts that are involved in protective mechanisms against irreversible ischemic damage. A preferred embodiment of the invention provides for a full-length sequence and characterization of an isolated nucleic acid, comprising a pDJA1 protein coding sequence. This nucleic acid, hereinafter referred to as pDJA1, has been identified as a cardiac-specific pDna1 co-chaperone and comprises the sequence of SEQ ID NO: 1, and recombinant DNA molecules, cloned genes, degenerate variants, mutants, analogs, or fragments thereof. This transcript is characterized by a remarkable tissue distribution and by a strong upregulation during ischemia/reperfusion. A yet further embodiment of the invention provides for an isolated polypeptide, comprising an amino acid sequence of a pDJA1 protein. The polypeptide comprises the amino acid sequence of SEQ ID NO: 2, and fragments, mutants, variants, analogs or derivatives thereof.

In a further embodiment of the invention, the nucleic acid sequence of the invention may be operatively linked to an expression control sequence and may be introduced into an appropriate host or host cell. The invention accordingly extends to unicellular hosts transformed with the cloned gene or recombinant DNA molecule comprising a DNA sequence encoding the present invention, and more particularly, the DNA sequences or fragments thereof determined from the sequences set forth above. In a further embodiment, the nucleic acid sequence of SEQ ID NO: 1, or other genes encoding a protein with similar activity, including cytoprotective capacity, may be introduced into a host cell, including but not limited to cardiac cells or neuronal stem cells, and said cells are transplanted to the site of injury in an animal in need of such therapy. In a preferred embodiment, the animal is a human subject.

A twelfth aspect of the invention provides for transgenic non-human animals (e.g., mice, rats, goats, sheep, pigs) that express the genes and gene products of the present invention which have the preferred activity. A preferred embodiment is a transgenic animal having pDJA1 nucleic acids and proteins encoded by a transgene. Transgenic, non-human knockout animals (e.g., mice), and a pDJA1 gene and variants thereof are also provided.

A thirteenth aspect of the invention is the use of the genes and gene products of the present invention, or use of agents that upregulate expression and/or activity of these genes and gene products for treatment of central nervous system (CNS) disorders, including but not limited to stroke, Alzheimer's disease, acute and chronic spinal cord injuries, traumatic brain injuries and other CNS disorders.

A fourteenth aspect of the invention provides a method of determining if a subject is at risk for developing cardiovascular disease, said method comprising:

(I) measuring an amount of an pDJA1 gene or gene product in a tissue sample derived from the subject, wherein said pDJA1 gene or gene product is:

(a) a DNA corresponding to SEQ ID NO: 1, or a nucleic acid derived therefrom;

(b) a protein comprising SEQ ID NO: 2;

(c) a nucleic acid comprising a sequence hybridizable to SEQ ID NO: 1, or its complement under conditions of high stringency, or a protein comprising a sequence encoded by said hybridizable sequence;

(d) a nucleic acid at least 90% homologous to SEQ ID NO: 1, or its complement as determined using the NBLAST algorithm; or a protein encoded thereby; and (II) comparing the amount of said pDJA1 gene product in the subject with the amount of pDJA1 gene product present in a non-ischemic cardiac tissue sample or predetermined standard for a nonischemic cardiac tissue sample, wherein an elevated amount of said pDJA1 gene product in the subject compared to the amount in the non-iscehmic cardiac tissue sample or pre-determined standard for a non-ischemic cardiac tissue sample indicates a risk of developing cardiovascular disease in the subject.

A fifteenth aspect of the invention provides a method for screening, diagnosis or prognosis of a cardiovascular condition selected from the group consisting of atherosclerosis, coronary artery disease, ischemic heart disease, myocardial infarction, angina, stroke and other related conditions related to or resulting from an ischemic event, said method comprising:

(I) measuring an amount of an pDJA1 gene or gene product in a tissue sample derived from the subject, wherein said pDJA1 gene or gene product is:

(a) a DNA corresponding to SEQ ID NO: 1, or a nucleic acid derived therefrom;

(b) a protein comprising SEQ ID NO: 2;

(c) a nucleic acid comprising a sequence hybridizable to SEQ ID NO: 1, or its complement under conditions of high stringency, or a protein comprising a sequence encoded by said hybridizable sequence;

(d) a nucleic acid at least 90% homologous to SEQ ID NO: 1, or its complement as determined using the NBLAST algorithm; or a protein encoded thereby; and (II) comparing the amount of said pDJA1 gene product in the subject with the amount of pDJA1 gene product present in a non-ischemic cardiac tissue sample or predetermined standard for a nonischemic cardiac tissue sample, wherein an elevated amount of said pDJA1 gene product in the subject compared to the amount in the non-iscehmic cardiac tissue sample or pre-determined standard for a non-ischemic cardiac tissue sample indicates a risk of developing cardiovascular disease in the subject.

In accordance with a proposed classification of HSP40 homologues (Ohtsuka, K., et al., Mammalian HSP40/DNAJ homologs: cloning of novel cDNAs and a proposal for their classification and nomenclature, *Cell Stress Chaperones*, (2000); 5: 98–112), this transcript has been designated pDJA1, for pig DJA1-like protein A1. Upregulation of pDJA1 during reperfusion further expands the concept of a program for cell survival that prevents irreversible damage in post-ischemic myocardium.

Other objects and advantages will become apparent from a review of the ensuing detailed description and attendant claims. All references cited in the present application are incorporated herein in their entirety.

BRIEF DESCRIPTION OF THE FIGURES

FIGS. 1A, 1B, 1C. Nucleotide and amino acid sequence of pDJA1. The figure shows the full-length transcript encoding pDJA1. The N-terminal J domain and the C-terminal prenylation site are boxed. The four zinc fingers motifs are underlined with a solid line. The glycine-phenylalanine stretch is underlined with a dotted line. The AU-rich motifs in the 3'UTR are shadowed. The poly-A signal is underlined with an arrow. The nucleic acid sequence of pDJA1 is designated as SEQ ID NO: 1. The corresponding protein sequence of pDJA1 is designated as SEQ ID NO: 2.

FIG. 2. Protein sequence alignment between the prototypic human HSP40 (acc. BC002352) and pDJA1. The alignment shows that both molecules are highly similar in the N-terminal part, which includes the J domain and the G/F tract. PDJA1 markedly diverges from, and is longer than, HSP40 in its C-terminal part. The protein sequence of HSP40 is designated as SEQ ID NO: 3. The corresponding sequence alignment of pDJA1 is designated as SEQ ID NO: 4.

FIG. 5. Upregulation of pDJA1 gene expression by ischemia/reperfusion. Panel A shows the expression of pDJA1 measured by Northern blot in left ventricular samples from four hearts submitted to regional ischemia for 90 min, followed by 1 hour reperfusion. In each case, a sample from the remote area and from the ischemic area were measured in parallel. Normalization of the pDJA1 signal to the 28S rRNA signal showed that pDJA1 was increased 4-fold in stunned myocardium compared to remote area. *, P<0.05 versus remote. Panel B shows the quantitative measurement of the pDJA1 transcript in samples of the remote (open symbols) and stunned area (closed symbols), from hearts submitted to 90 min occlusion followed by no reperfusion, 1 h or 12 h reperfusion (n=5 in each group). The subendocardial (circles) and subepicardial areas (squares) were measured separately. *, P<0.05 versus corresponding value in remote myocardium. Panel C, in-situ hybridization (magnification, x40) showing that the expression of the pDJA1 gene in stunned myocardium is myocyte-specific.

DETAILED DESCRIPTION OF THE INVENTION

Figure 3:
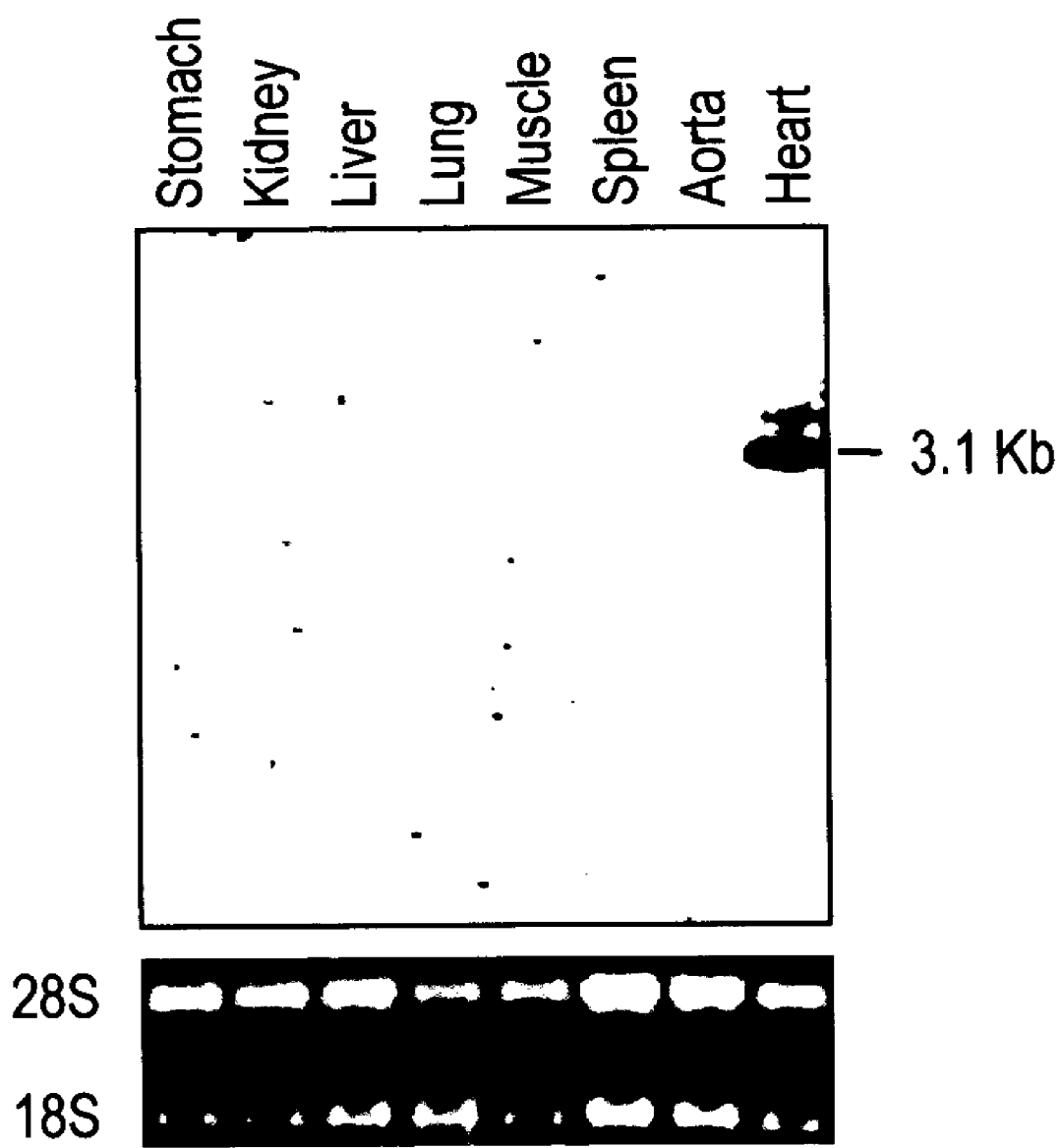
FIG. 3. Tissue distribution of pDJA1 in the swine. Northern blot performed on different pig tissues with a probe corresponding to a 0.8-KB fragment of pDJA1 found in the subtractive hybridization. Ribosomal RNAs (28S and 18S) are shown for equal loading.

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

DEFINITIONS

The terms used herein have the meanings recognized and known to those of skill in the art, however, for convenience and completeness, particular terms and their meanings are set forth below.

"Agent" refers to all materials that may be used to prepare pharmaceutical and diagnostic compositions, or that may be compounds, nucleic acids, polypeptides, fragments, isoforms, variants, or other materials that may be used independently for such purposes, all in accordance with the present invention.

The term "antibody" as used herein includes intact molecules as well as fragments thereof, such as Fab and F(ab')$_2$, which are capable of binding the epitopic determinant. Antibodies that bind the genes or gene products of the present invention can be prepared using intact polynucleotides or polypeptides or fragments containing small peptides of interest as the immunizing antigen attached to a carrier molecule. Commonly used carriers that are chemically coupled to peptides include bovine serum albumin and thyroglobulin. The coupled peptide is then used to immunize the animal (e.g, a mouse, rat or rabbit). The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397.). The antibody may be a human or a humanized antibody. The antibody may be prepared in mice, rats, goats, sheep, swine, dogs, cats, or horses.

A "therapeutically effective amount" is an amount sufficient to decrease or prevent the symptoms associated with the cardiac or other related conditions contemplated for therapy with the compositions of the present invention.

A "variant" (v) of polynucleotides or polypeptides, as the term is used herein, are polynucleotides or polypeptides that are different from a reference polynucleotide or polypeptide, respectively. Variant polynucleotides are generally limited so that the nucleotide sequence of the reference and the variant are closely related overall and, in many regions, identical. Changes in the nucleotide sequence of the variant may be silent. That is, they may not alter the amino acid sequence encoded by the polynucleotide. Where alterations are limited to silent changes of this type a variant will encode a polypeptide with the same amino acid sequence as the reference. Alternatively, changes in the nucleotide sequence of the variant may alter the amino acid sequence of a polypeptide encoded by the reference polynucleotide. Such nucleotide changes may result in amino acid substitutions, additions, deletions, fusions, and truncations in the polypeptide encoded by the reference sequence. Variant polypeptides are generally limited so that the sequences of the reference and the variant are that are closely similar overall and, in many regions, identical. For example, a variant and reference polypeptide may differ in amino acid sequence by one or more substitutions, additions, deletions, fusions, and truncations, which may be present or absent in any combination. Such variants can differ in their amino acid composition (e.g. as a result of allelic or natural variation in the amino acid sequence, e.g. as a result of alternative mRNA or pre-mRNA processing, e.g. alternative splicing or limited proteolysis) and in addition, or in the alternative, may arise from differential post-translational modification (e.g., glycosylation, acylation, phosphorylation, isoprenylation, lipidation).

"Gene Product" as used herein, unless otherwise indicated, is a protein or polypeptide encoded by the nucleic acid sequences identified by the methods of the present invention, including but not limited to SEQ ID NO: 2; a nucleic acid comprising a sequence hybridizable to SEQ ID NO: 1 or its complement under conditions of high stringency, or a protein comprising a sequence encoded by said hybridizable sequence; a nucleic acid at least 90% homologous to SEQ ID NO: 1 or its complement as determined using the NBLAST algorithm; a nucleic acid at least 90% homologous to SEQ ID NO: 1 or a fragment or derivative of any of the foregoing proteins or nucleic acids.

"Modulate" as used herein, refers to a compound or agent (including but not limited to proteins, polypeptides, or fragments thereof, nucleotides, nucleic acid fragments, synthetic organic compounds, antibodies) which are capable of increasing or decreasing the level and/or activity of a gene or gene product identified by the methods described herein, said genes or gene products having a beneficial effect in preventing cell death and/or irreversible damage in cardiovascular disease, or other diseases or conditions whereby ischemia results in damage to tissue, including heart tissue, brain tissue or other tissues affected by a lack of oxygen due to inadequate perfusion. These may include atheroslerosis or restenotic lesions, stroke, or anemia, to name a few non-limiting examples. Those skilled in the art, based on the present description, will understand that such modulation can be determined by assays and techniques known to those of skill in the art, including as described in more detail herein.

"Agonist" as used herein, refers to a compound or agent (including but not limited to proteins, polypeptides, or fragments thereof, nucleotides, nucleic acid fragments, synthetic organic compounds, antibodies) capable of increasing the level and/or activity of a pDJA1-like molecule or a variant thereof and may be referred to herein as an agonist.

"Analog" as used herein, refers to a nucleotide, a protein, or a polypeptide that possesses similar or identical activity or function(s) as the nucleotide, protein or polypeptide having the desired activity and therapeutic effect of the present invention (eg. protection of cells from death and/or prevention of irreversible damage in post-ischemic events in tissues), but need not necessarily comprise a sequence that is similar or identical to the sequence of the preferred embodiment, such as that of SEQ ID NOS: 1 and 2, or possess a structure that is similar or identical to that of SEQ ID NOS: 1 and 2. As used herein, a nucleic acid or nucleotide sequence, or an amino acid sequence of a protein or polypeptide is "similar" to that of a nucleic acid, nucleotide or protein or polypeptide having the desired activity if it satisfies at least one of the following criteria: (a) the nucleic acid, nucleotide, protein or polypeptide has a sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleic acid, nucleotide, protein or polypeptide sequences having the desired activity as described herein (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of the AAPI; or (c) the polypeptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding the polypeptides of the present invention having the desired therapeutic effect. As used herein, a polypeptide with "similar structure" to that of the preferred embodiments of the invention refers to a polypeptide that has a similar secondary, tertiary or quarternary structure as that of the preferred embodiment (eg. SEQ ID NO: 2). The structure of a polypeptide can determined by methods known to those skilled in the art, including but not limited to, X-ray crystallography, nuclear magnetic resonance, and crystallographic electron microscopy.

"Derivative" refers to either a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

The "percent identity" of two amino acid sequences or of two nucleic acid sequences can be or is generally determined by aligning the sequences for optimal comparison purposes (e.g., gaps can be introduced in either sequences for best alignment with the other sequence) and comparing the amino acid residues or nucleotides at corresponding positions. The "best alignment" is an alignment of two sequences that results in the highest percent identity. The percent identity is determined by the number of identical amino acid residues or nucleotides in the sequences being compared (i.e., % identity=# of identical positions/total # of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264–2268, modified as in Karlin and Altschul (1993) Proc. Natl. Acad. Sci. USA 90:5873–5877. The NBLAST and XBLAST programs of Altschul, et al. (1990) J. Mol. Biol. 215:403–410 have incorporated such an algorithm. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov.

Another example of a mathematical algorithm utilized for the comparison of sequences is the algorithm of Myers and Miller, CABIOS (1989). The ALIGN program (version 2.0) which is part of the GCG sequence alignment software package has incorporated such an algorithm. Other algorithms for sequence analysis known in the art include ADVANCE and ADAM as described in Torellis and Robotti (1994) Comput. Appl. Biosci., 10 :3–5; and FASTA described in Pearson and Lipman (1988) Proc. Natl. Acad. Sci. 85:2444–8. Within FASTA, ktup is a control option that sets the sensitivity and speed of the search.

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

"Treatment" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

In accordance with a proposed classification of HSP40 homologues (Ohtsuka, K., et al., Mammalian HSP40/DNAJ homologs: cloning of novel cDNAs and a proposal for their classification and nomenclature, *Cell Stress Chaperones*, (2000); 5: 98–112), the transcript of the present invention has been designated pDJA1, for pig DJA1-like protein A1.

General Description

The present invention relates to the discovery that a gene, pDJA1 and variants thereof, have an expression pattern that is up-regulated in cardiac tissue following a period of ischemia followed by reperfusion, and in cardiac cell lines. The invention relates to the use of said gene, gene products, and agonists of said gene or gene products (pDJA1 and variants thereof, cDNA, RNA, and/or protein, small synthetic organic molecules, antibodies) as targets for diagnosis, drug screening and therapies for cardiovascular diseases. In a preferred embodiment, the invention provides for methods of using the protein and variants thereof, or nucleic acids that encode said proteins for the treatment, prevention and diagnosis of cardiovascular disease.

In particular, the methods of the present invention include using nucleic acid molecules that encode the pDJA1 protein and variants thereof, and recombinant DNA molecules, cloned genes or degenerate variants thereof, and in particular naturally occurring variants that encode pDJA1 related gene products. The methods of the present invention additionally include using cloning vectors, including expression vectors, containing the nucleic acid molecules encoding pDJA1 and variants thereof, and hosts that contain such nucleic acid molecules. The methods of the present invention also encompass the use of pDJA1 gene products and variants thereof, including fusion proteins, and antibodies directed against such pDJA1 gene products or conserved variants or fragments thereof.

This novel gene, designated "pDJA1", which has been cloned, was identified using subtractive hybridization between stunned and normal heart tissue in a pig model for ischemia/reperfusion. This gene is expressed in heart tissue which was transiently deprived of oxygen (ischemia) followed by reperfusion. The 0.8-kb fragment, which was subcloned did not match any known transcript in public databases. Further studies that were done to determine the full-length sequence of the novel gene, identified the cDNA as being 3.1-kb long and characterized by a 62 nucleotide long 5'-UTR, a 397 amino acid open reading frame and a 1.75 kb long 3'-UTR. Furthermore, the open reading frame begins with an ATG nucleotide at nucleotide 63, and is not preceded by a Kozak's consensus for translation initiation. The protein encoded by this nucleic acid has an apparent molecular weight of 44.7 kDa and a pI=8.27. The nucleic acid sequence of this novel gene is found in SEQ ID NO: 1. The corresponding amino acid sequence encoded by this gene is found in SEQ ID NO: 2.

pDJA1 as described herein, is a novel heart-specific ventricle-enriched cardioprotective co-chaperone, which participates in the program of cell survival that limits irreversible damage in post-ischemic myocardium. The findings in the present application suggest that this gene, its gene product, and other agents or agonists that have the same activity and/or function in a similar manner may prove to be useful in the treatment of cardiovascular disease, ischemic heart disease, myocardial infarct or related disorders.

Furthermore, the genes, gene products, or other agents or agonists may also prove useful in a diagnostic setting in order to monitor patients believed to have experienced a myocardial infarct or ischemic cardiac event or other related cardiac condition, and may be used in a prognostic manner to determine the potential for subsequent ischemic cardiac events. A search for agonists of this gene may prove to be a useful strategy for identifying a new class of cardioprotective agents and treatment modalities.

Thus, the present invention further relates to methods for the diagnostic evaluation and prognosis of cardiovascular disease in a subject animal. Preferably the subject is a mammal, more preferably the subject is a human. In a preferred embodiment the invention relates to methods for diagnostic evaluation and prognosis of cardiovascular disease. For example, nucleic acid molecules of the invention can be used as diagnostic hybridization probes or as primers for diagnostic PCR analysis for detection of abnormal expression of the pDJA1 gene.

Antibodies or other binding partners to pDJA1 and variants thereof can be used in a diagnostic test to detect the presence of the pDJA1 gene or gene product in body fluids, cells or in tissue biopsy. In specific embodiments, measurement of serum or cellular pDJA1 gene products and variants thereof can be made to detect cellular and/or tissue damage following a myocardial infarct, a stroke, or other related cardiovascular diseases or conditions.

The present invention also relates to methods for the identification of subjects having a predisposition to cardiovascular disease, or alternatively, being at risk for a second myocardial infarct or stroke or related condition. The subject can be any animal, but preferably the subject is a mammal, and most preferably the subject is a human. In a non-limiting example nucleic acid molecules of the invention can be used as diagnostic hybridization probes or as primers for quantitative reverse transcriptase-PCR (RT-PCR) analysis to determine expression levels of the pDJA1 gene or gene product and variants thereof. In another example, nucleic acid molecules of the invention can be used as diagnostic hybridization probes or as primers for diagnostic PCR analysis for the identification of pDJA1 and variants thereof, naturally occurring or non-naturally occurring gene mutations, allelic variations and regulatory defects in the pDJA1 gene.

In a preferred embodiment, the present invention further provides methods of determining if a subject is at risk for developing cardiovascular disease, said method comprising (I) measuring an amount of an pDJA1 gene product in a sample derived from the subject, wherein said pDJA1 gene product is: (a) an DNA corresponding to SEQ ID NO: 1, or a nucleic acid derived therefrom; (b) a protein comprising SEQ ID NO: 2; (c) a nucleic acid comprising a sequence hybridizable to SEQ ID NO: 1, or its complement under conditions of high stringency, or a protein comprising a sequence encoded by said hybridizable sequence; (d) a nucleic acid at least 90% homologous to SEQ ID NO: 1, or its complement as determined using the NBLAST algorithm; or a protein encoded thereby; and (II) comparing the amount of said pDJA1 gene product in the subject with the amount of pDJA1 gene product present in a non-ischemic cardiac tissue sample or predetermined standard for a nonischemic cardiac tissue sample, wherein an elevated amount of said pDJA1 gene product in the subject compared to the amount in the non-iscehmic cardiac tissue sample or predetermined standard for a non-ischemic cardiac tissue sample indicates a risk of developing cardiovascular disease in the subject.

Imaging methods, for imaging the localization and/or amounts of pDJA1 gene products in a patient, are also provided for diagnostic and prognostic use.

Screening Assays

Intensive and systematic evaluation of gene expression patterns is essential in understanding the physiological mechanisms associated with cell death and/or cellular responsiveness to the events leading to cell death or tissue damage following an ischemic cardiac episode. Several techniques that permit comparison of gene expression in normal and damaged cells are known in the art. Examples of these techniques include: Serial Analysis of Gene Expression (SAGE) (Velculescu et al., 1995, Science 270:484); Restriction Enzyme Analysis of Differentially Expressed Sequences (READS) (Prasher et al., 1999, Methods in Enzymology 303:258); Amplified Fragment Length Polymorphism (AFLP) (Bachem et al., 1996, Plant Journal 9:745); Representational Difference Analysis (RDA) (Hubank et al., 1994, Nucleic Acid Research 22:(25):5640); differential display (Liang et al, 1992, Cancer Research 52(24):6966); and suppression subtractive hybridization (SSH) (Diatchenko et al., 1996, Proc. Natl. Acad. Sci. USA 93:6025). The use of such differential expression methods have led the present inventors to the identification and characterization of the pDJA1 gene, as a gene whose expression is associated with heart tissue damaged by a transient period of ischemia followed by reperfusion. This discovery by the present inventors has made possible the use of pDJA1 and variants thereof for the treatment, prevention and diagnosis of cardiovascular disease, including but not limited to atherosclerosis, coronary artery disease, ischemic heart disease, myocardial infarct, stroke and other related conditions.

Hybridization Conditions

A nucleic acid which is hybridizable to an PDJA1 nucleic acid (e.g., having a sequence as set forth in SEQ ID NO: 1, or to its reverse complement, or to a nucleic acid encoding an PDJA1 derivative, or to its reverse complement under conditions of low stringency can be used in the methods of the invention to detect the presence of an PDJA1 gene and/or presence or expression level of an PDJA1 gene product. By way of example and not limitation, procedures using such conditions of low stringency are as follows (see also Shilo and Weinberg, 1981, Proc. Natl. Acad. Sci. U.S.A. 78, 6789–6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10⁶ cpm ³²P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency that may be used are well known in the art (e.g., as employed for cross-species hybridizations).

A nucleic acid which is hybridizable to an PDJA1 nucleic acid (e.g., having a sequence as set forth in SEQ ID NO: 1 or to its reverse complement, or to a nucleic acid encoding an PDJA1 derivative, or to its reverse complement under conditions of high stringency) is also provided for use in the methods of the invention. By way of example and not limitation, procedures using such conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10⁶ cpm of ³²P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency that may be used are well known in the art.

A nucleic acid which is hybridizable to an PDJA1 nucleic acid (e.g., having a sequence as set forth in SEQ ID NO: 1 or to its reverse complement, or to a nucleic acid encoding an PDJA1 derivative, or to its reverse complement under conditions of moderate stringency) is also provided for use in the methods of the invention. For example, but not limited to, procedures using such conditions of moderate stringency are as follows: filters comprising immobilized DNA are pretreated for 6 hours at 55° C. in a solution containing 6×SSC, 5× Denhardt's solution, 0.5% SDS and 100 µg/ml denatured salmon sperm DNA. Hybridizations are carried out in the same solution with 5–20×10⁶ cpm ³²P-labeled probe. Filters are incubated in hybridization mixture for 18–20 hours at 55° C., and then washed twice for 30 minutes at 60° C. in a solution containing 1×SSC and 0.1% SDS. Filters are blotted dry and exposed for autoradiography. Washing of filters is done at 37° C. for 1 hour in a solution containing 2×SSC, 0.1% SDS. Other conditions of moderate stringency that may be used are well known in the art. (see, e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987–1997 Current Protocols,© 1994–1997 John Wiley and Sons, Inc.).

The invention provides methods for identifying agents (e.g., chemical compounds, carbohydrates, proteins, peptides, antibodies or nucleotides) that enhance the expression and/or activity of pDJA1 gene or gene products. The invention also provides methods of identifying agents, candidate compounds or test compounds that specifically bind to pDJA1. Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683, each of which is incorporated herein in its entirety by reference).

In one embodiment, agents that interact with (i.e., bind to) pDJA1 or a polypeptide or fragment (e.g. a functionally active fragment), are identified in a cell-based assay system. In accordance with this embodiment, cells expressing pDJA1 comprising an PDJA1 peptide or polypeptide, a fragment thereof, are contacted with a candidate compound or a control compound and the ability of the candidate compound to interact with pDJA1 is determined. If desired, this assay may be used to screen a plurality (e.g., a library) of candidate compounds. The cell, for example, can be of prokaryotic or eukaryotic origin (e.g., E. coli or CHO cells), and may contain the pDJA1 peptide or polypeptide, fragment, or related polypeptide thereof. In some embodiments, the pDJA1 gene or pDJA1 polypeptide, fragment, or related polypeptide thereof or the candidate compound is labeled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between a pDJA1 and a candidate compound. The ability of the candidate compound to interact directly or indirectly with the pDJA1 can be determined by methods known to those of skill in the art. For example, the interaction can be determined by flow cytometry, a scintillation assay, immunoprecipitation or western blot analysis.

In another embodiment, agents interact with (i.e., bind to) the pDJA1 gene or gene product in a cell-free assay system. In accordance with this embodiment, pDJA1 is contacted with a candidate compound or a control compound and the ability of the candidate compound to interact with the pDJA1 is determined. If desired, this assay may be used to screen a plurality (e.g. a library) of candidate compounds. In one embodiment, the pDJA1 gene or gene product is first immobilized, by, for example, contacting the pDJA1 with an immobilized antibody which specifically recognizes and binds it, or by contacting a purified preparation of the pDJA1 with a surface designed to bind nucleic acids or proteins. The pDJA1 may be partially or completely purified (e.g., partially or completely free of other nucleic acids or polypeptides) or part of a cell lysate. The ability of the candidate compound to interact with the pDJA1 can be determined by methods known to those of skill in the art.

In another embodiment, a cell-based assay system is used to identify agents that bind to or modulate the expression or activity of the pDJA1 gene or gene product, or a biologically active portion thereof. In a primary screen, a plurality (e.g., a library) of compounds are contacted with cells that naturally express pDJA1 in order to identify compounds that modulate the expression and/or activity of the pDJA1. The ability of the candidate compound to modulate the expression and/or activity of the pDJA1 can be determined by methods known to those of skill in the art, including without limitation, flow cytometry, a scintillation assay, immunoprecipitation and western blot analysis.

In another embodiment, agents that modulate (i.e., up-regulate or down-regulate) the expression and/or activity of PDJA1 are identified by contacting cells (e.g., cells of prokaryotic or eukaryotic origin) containing the components capable of forming an active pDJA1 with a candidate compound or a control compound (e.g., phosphate buffered saline (PBS)) and determining the expression and/or activity of the pDJA1. The level of pDJA1 expression and/or PDJA1 activity in the presence of the candidate compound is compared to the level of expression or activity in the absence of the candidate compound (e.g., in the presence of a control compound). The candidate compound can then be identified as a modulator of the expression and/or assembly of the pDJA1 based on this comparison. For example, when presence of an active pDJA1 is significantly greater in the presence of the candidate compound than in its absence, the candidate compound is identified as a stimulator of pDJA1 expression/formation and/or an enhancer of pDJA1 activity. Alternatively, when presence of an active pDJA1 is significantly less in the presence of the candidate compound than in its absence, the candidate compound is identified as an inhibitor of pDJA1 expression/formation and/or inhibitor of pDJA1 activity.

In another embodiment, agents that modulate (i.e., upregulate or down-regulate) the expression, activity or both, of pDJA1 are identified in an animal model. Examples of suitable animals include, but are not limited to, mice, rats, pigs, rabbits, monkeys, guinea pigs, dogs and cats. Preferably, the animal used represents a model of a pDJA1-associated cardiovascular disease, such as ischemic heart disease, stroke, myocardial infarct.

In accordance with this embodiment, the test compound or a control compound is administered (e.g. orally, intravenously, intramuscularly, subcutaneously, intrathecally, rectally) to a suitable animal and the effect on the expression or activity or both expression and activity of the pDJA1 is determined, or the effect on an pDJA1-bearing target cell is determined. Changes in the expression and/or activity of pDJA1 can be assessed by any suitable method described above, based on the present description.

This invention further provides novel agents identified by the above-described screening assays and uses thereof for treatments as described herein.

Therapeutic Uses of the Invention

Another aspect of the invention provides for the use of pDJA1 genes or gene products and proteins or polypeptides, or agonists thereof in prevention of cell death in vitro and in vivo. One embodiment of the invention features use of the genes and/or gene products, protein, polypeptides, small molecule agonists to prevent or reverse tissue damage in the heart of a subject having or prone to having cardiovascular disease. The agonists of pDJA1 expression and/or activity are envisioned to be small molecule inhibitors, peptides, polypeptides, antibodies, antibody fragments or mimics thereof.

The invention provides for treatment or prevention of various cardiac diseases and disorders by administration of a therapeutic agent. Such agents include but are not limited to: agents which enhance expression, formation or activity of pDJA1, agents which modulate the activity of pDJA1, agents able to act as agonists of pDJA1, and related analogs, derivatives, and fragments thereof. Such agonists may include small molecule agonists.

In one embodiment wherein expression and/or activity of pDJA1 is desirable, one or more agents that upregulate pDJA1 gene expression and/or gene or gene product activity, are administered alone or in combination with one or more additional therapeutic compounds or treatments. In a preferred embodiment, an upregulator of PDJA1 gene or gene product activity is administered to a human subject for therapy (e.g. to ameliorate symptoms or to retard onset or progression) of cardiovascular disease.

Assays for Therapeutic Compounds

The present invention also provides for assays for use in discovery of pharmaceutical products in order to identify or verify the efficacy of compounds for treatment or prevention of cardiovascular diseases in which pDJA1 may prove efficacious. In one embodiment, agents can be assayed for their ability to inhibit cell death in vitro or in vivo. Compounds able to enhance expression or activity of pPDJA1 in vitro can be further tested for in vivo activity in experimental animal models of cardiovascular disease and can be used as lead compounds for further drug discovery, or used therapeutically.

In various embodiments, in vitro assays can be carried out with cardiac cells, containing the pDJA1 gene and which are representative of the cell type involved in a subject's disease, to determine if a compound has a desired effect upon such cell types. In one embodiment, the cells are derived from cardiac tissue, such as myocytes.

Compounds for use in therapy can be tested in suitable animal model systems prior to testing in humans, including but not limited to rats, mice, pigs, chicken, cows, monkeys, rabbits, etc. For in vivo testing, prior to administration to humans, any animal model system known in the art may be used. In one embodiment, test compounds that modulate the expression or activity of pDJA1 are identified in non-human animals (e.g., mice, rats, pigs, monkeys, rabbits, and guinea pigs), preferably non-human animal models for cardiovascular diseases. In accordance with this embodiment, a test compound or a control compound is administered to the animals, and the effect of the test compound on pDJA1 levels or activity is determined in cells obtained from the animal. A test compound that alters the level or activity of pDJA1 can be identified by comparing the level of the selected pDJA1 in a cell culture obtained from an animal or group of animals treated with a test compound with the level of the pDJA1 in a cell culture obtained from an animal or group of animals treated with a control compound.

In yet another embodiment, test compounds that modulate the level or activity of pDJA1 are identified in human subjects having a cardiovascular disease or condition associated with expression of pDJA1. In accordance with this embodiment, a test compound or a control compound is administered to the human subject, and the effect of a test compound on either reduction in damage to heart tissue, or amelioration of symptoms associated with the disease is determined by methods known in the art.

Therapeutic and Prophylactic Compositions and Their Use

The invention provides methods of treatment comprising administering to a subject an effective amount of an agent of the invention. In a preferred aspect, the compound is substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject.

Various delivery systems are known and can be used to administer a compound of the invention, e.g., encapsulation in liposomes, microparticles, or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment.

Another aspect of the invention provides for pharmaceutical compositions comprising purified pDJA1 enhancers for therapeutic use in treatment of cardiovascular diseases. One embodiment features treatment of a wide range of cardiovascular diseases or conditions with pharmaceutical compositions containing acceptable carriers and excipients.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the compound of the invention which will be effective in the treatment of cardiovascular diseases can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In a specific embodiment, it may be desirable to administer the pharmaceutical compositions of the invention locally to the area in need of treatment; this may be achieved, for example, and not by way of limitation, by local infusion during surgery, by topical application, by injection, by means of a catheter, or by means of an implant, said implant being of a porous, non-porous, or gelatinous material, including membranes, such as sialastic membranes, or fibers or co-polymers such as Elvax (see Ruan et al, 1992, Proc Natl Acad Sci USA, 89:10872–10876). In one embodiment, administration can be by direct injection by aerosol inhaler.

In another embodiment, the compound can be delivered in a vesicle, in particular a liposome (see Langer (1990) Science 249:1527–1533; Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 3. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115–138). Other suitable controlled release systems are discussed in the review by Langer (1990) Science 249:1527–1533.

EXAMPLES

Animal Model for Ischemia/Reperfusion

Female domestic swine (22–25 kg) were anesthetized with thiopental sodium (5–10 mg/kg, i.v.) and isoflurane (0.5–1.5 vol %). A left thoracotomy was performed through the fifth intercostal space to expose the heart[16]. A hydraulic occluder was implanted around the base of the left anterior descending (LAD) artery. Myocardial blood flow through the LAD was monitored by a Doppler flow probe. After 3 days of recovery, stunning was induced in the conscious animal by inflating the coronary occluder, to reduce the blood flow in the LAD by 40%. Reduction of the blood flow was controlled on-line via the flow probe. The coronary stenosis was maintained for 90 min, followed by deflation of the occluder and full reperfusion. Animals were anesthetized at the end of the 90 min-stenosis period (n=5), or after 1 h (n=5) and 12 h (n=5) reperfusion. In each case, myocardial samples were taken from both the stunned area (centrally in the LAD territory) and the remote area of the beating heart. Each sample was further separated in a subendocardial and a subepicardial portion. Three instrumented pigs, in which no occlusion was performed, were used as shams. Samples from both atria and from different organs (kidney, liver, lung, spleen, aorta, skeletal muscle, stomach) were taken as well. The samples were frozen in liquid nitrogen or fixed in fresh 4% paraformaldehyde. The investigation conforms with the *Guide for the Care and Use of Laboratory Animals* published by the US National Institute of Health (NIH Publication No 85–23, revised 1996).

Cloning of RNA Extraction

About 300 mg of each sample was homogenized in 3 ml of the guanidium thiocyanate-phenolchloroform solution (Triazol, Gibco Life Technologies). Total RNA was extracted (Chomczynski, P., et al., Single-step method of RNA isolation by acid guanidium thiocyanate-phenol-chloroform extraction, *Anal Biochem.*, (1987); 162: 159–169), resuspended in 50 µl DEPC-water, and its concentration was measured spectrophotometrically by the absorbance at 260 nm. The integrity of the RNA pool was checked on a 1%-agarose denaturing gel stained with ethidium bromide.

Cloning Protocol for PDJA1

A pig heart cDNA library was subcloned in the pCMV Sport6 vector (Life Technologies) and used for screening with primers designed from the sequence obtained in the subtractive hybridization. The cDNA was obtained by PCR cloning and colony hybridization. The 5' end of the transcript was obtained by 5'RACE after decapping of the transcripts (First Choice RLM-RACE, Ambion). PCR products were sequenced by triple pass on a 3100 Genetic Analyzer (Applied Biosystems) using the Big-Dye Terminator (Applied Biosystems). Data analysis was performed with the ABI AutoAssembler software. Gene analysis and sequence comparisons were performed with the MacVector software.

Northern Blotting

Fifteen micrograms of total RNA was applied on a 1.2%-agarose denaturing gel stained with ethidium bromide. After migration, the RNA was transferred overnight to a nylon Hybond-N membrane (Amersham Pharmacia), then cross-linked by UV. A probe was derived as an isolated restriction fragment from the subtractive library, heat-denatured, and labeled with [$\alpha^{32}$P]-dCTP (Prime-It II kit, Stratagene). Hybridization was performed overnight at 42° C. in a hybridization solution containing 50% formamide. Intensity of the radioactive signal was measured with the Multi-Analyst detection system (Biorad). RNA integrity was controlled by comparison of the bands corresponding to the 28S and 18S rRNAs.

Quantitative RT-PCR

Expression of pDJA1 was measured by quantitative RT-PCR on a 7700 Sequence Detector (Applied Biosystems) with specific primers (forward: 5'-CTCTCTTGGAAGCT-TCCTGAAC-3' (SEQ ID NO: 5), REVERSE: 5'-GCACT-GCAAAGGCTGTCAA-3' (SEQ ID NO: 6)) and a fluorescent probe (5'FAM-AAGCTTGTGGTGAGGACAAACCAGTGTTT-3'TAMRA (SEQ ID NO: 7)). The mRNA of interest was reverse-transcribed from 60 nanograms of total RNA, and subsequently used for quantitative 2-step PCR (40 cycles of a 10 sec-step at 95° C. and a 1 min-step at 60° C.). Internal RNA standards were prepared from the PCR-amplified cDNA after ligation of the T7 promoter using the MegaShortScript kit (Ambion, Austin, Tex.) (Depre, C., et al., Unloaded heart in vivo replicates fetal gene expression cardiac hypertrophy, *Nature Medicine*, (1998); 4: 1269–1275). The values of the transcript were normalized to the transcript level of cyclophilin, measured in each sample as an internal control.

In-situ Hybridization

Samples were fixed in 4% paraformaldehyde/PBS, embedded in paraffin and sectioned at 6-μm intervals. Sections were dewaxed, rehydrated in ethanol, and treated with 0.8% pepsin in 0.2N HCl (DAKO) for 5 min at 37° C., followed by a 5-min rinse in $H_2O$. Sections were then re-fixed for 20 min in 4% paraformaldehyde dissolved in PBS. After washing, sections were acetylated in 0.25% acetic anhydride diluted in 0.1M triethanolamine buffer (pH=8.0). Sections were hybridized overnight at 37° C. in a humidified chamber with a biotin-labeled oligonucleotide probe diluted in hybridization solution (DAKO), corresponding to the same probe as the one used for the quantitative PCR. Probe hybridization was detected with streptavidin/alkaline phosphatase, after addition of BCIP/NBT as a chromogenic substrate (DAKO).

cDNA Subtractive Hybridization

Total RNA was first extracted (Williams, R. et al. J. Clin. Invest. (2000), 106:813–818) from both ischemic and control areas of two hearts submitted to 90-min occlusion and 1-h reperfusion. Messenger RNA was isolated, and 2 mg was used for first-strand cDNA synthesis with random primers. The subtractive hybridization was performed with the PCR-select cDNA subtraction kit (CLONTECH), following the manufacturer's recommendations. After second-strand synthesis, the two cDNA libraries were digested with RsaI. Digestion products of the "tester" library were ligated to a specific adapter (T7 promoter), then hybridized with a 30-fold excess of the "driver" library for subtraction. After hybridization, the remaining products were further amplified by PCR. In the forward subtraction, which determines the genes that are over-expressed in the ischemic sample, the ischemic tissue is the "tester" and the remote sample is the "driver." In the reverse subtraction, the "tester" and the "driver" are switched to determine the genes that are down-regulated in the ischemic sample. PCR-amplified subtracted products were subcloned into the pGEM-Teasy vector (Promega) and transformed into SURE2 cells (Stratagene). The clones were sequenced by standard procedure (ABI-Prizm 377 DNA sequencer, Applied Bio-systems). Sequences were queried in public databases to determine the identity of the genes.

Statistical Analysis

Data are expressed as mean±standard deviation. The number of samples in each experiment is indicated in the figure legends. Statistical analysis was performed with the Student's t test. A value of $P<0.05$ was considered as significant.

RESULTS

Cloning of pDJA1

Figure 2:
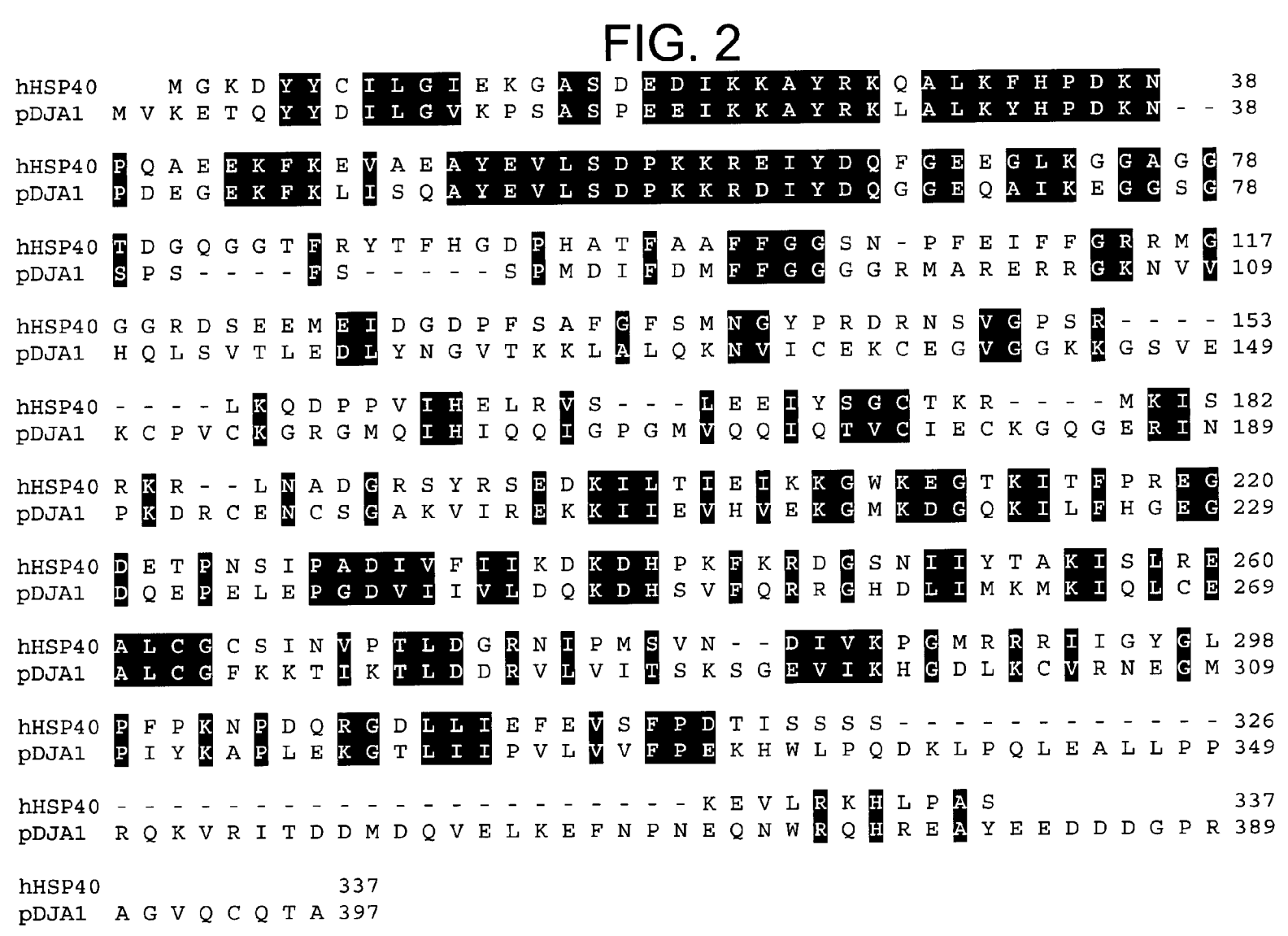

In addition to the known genes that were found in the subtractive hybridization between stunned and normal pig myocardium (Depre, C., et al., Gene program for cardiac cell survival induced by transient ischemia in conscious pig, *Proc. Nat'l Acad. Sci U.S.A.*, (2001); 98: 9336–9341), a 0.8 Kb cDNA fragment was subcloned which did not match any known transcript in public databases. To determine the full-length sequence of this unknown transcript, we screened a pig heart library with primers designed from the 0.8 Kb fragment, and amplified the products by PCR. With this method, 685 nucleotides of the 3'-end including a poly-adenylation signal and the poly-A tail were obtained. Next, we used 5'RACE PCR to obtain the remaining 5'end portion of the transcript. Taken together, a full-length transcript corresponding to a 3.1 Kb-long cDNA was obtained (FIG. 1A, 1B, 1C), which is characterized by a 62 nucleotide-long 5'-UTR, a 397 amino acid-open reading frame and a 1.75 Kb-long 3'-UTR. The open reading frame begins with the ATG at nucleotide 63, and is not preceded by a Kozak's consensus for translation initiation (Kozak, M., Point mutations define a sequence flanking the AUG initiator codon that modulates translation by eukaryotic ribosomes, *Cell*, (1986); 44: 283292). The protein has an apparent molecular weight of 44.7 KDa and a pI=8.27. The protein contains the N-terminal J domain characteristic of the DnaJ-like/HSP40 homologues, followed by a glycine-rich stretch and four "zinc finger" CxxCxGxG motifs. Interestingly, the C-terminus contains a CaaX prenylation site, which usually characterizes proteins involved in cell growth. The long 3'-UTR contains 7 AU-rich mRNA decay elements (Chen, C., et al., Selective degradation of early-response genes mRNAs: functional analyses of sequence features of the AU-rich elements, *Mol Cell Biol.* (1994); 14: 8471–8482), characterized by the sequence AUUUA. This sequence interacts with RNA-binding proteins, which regulate the stability and half-life of transcripts usually encoding proto-oncogenes and cytokines (Chen, C., et al., mRNA decay mediated by two distinct AU-rich elements from c-fos and granulocyte-macrophage colony-stimulating factor transcripts, different deadenylation kinetics and uncoupling from translation, *Mol Cell Biol.*, (1995); 15: 5777–5788). The 3'UTR ends with a poly-adenylation signal at nucleotide 2980. FIG. 2 shows the protein sequence alignment between pDJA1 and the human HSP40. Both proteins share a homologous N-terminus, which includes the J domain and the G/F tract. pDJA1 totally diverges from HSP40 in its C-terminal part, including the prenylation site which is absent in HSP40 (FIG. 2).

Tissue Distribution of pDJA1

Figure 4A:
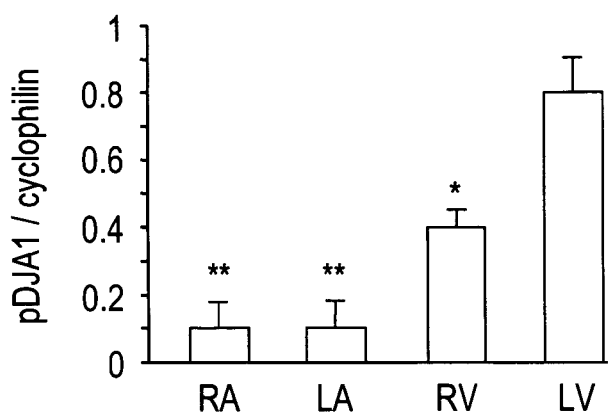
FIG. 4. Characterization by quantitative PCR of the expression of pDJA1 compared to other heat-shock proteins in the normal swine heart. Panel A shows the measurement of the pDJA1 transcript by quantitative PCR in the different cardiac chambers (n=4 per group). **, P<0.01 versus both ventricles; *, P<0.05 versus left ventricle. Panel B shows the different expression of pDJA1 between sub-endocardium (sub-endo) and sub-epicardium (sub-epi) in left ventricle (n=4 per group). *, P<0.05 versus sub-endocardium. Panel C shows that the expression of other heat-shock proteins, such as HSP70 and HSP40, does not differ transmurally in normal left ventricle (n=4 per group). Cyclophilin mRNA was used as a normalizer.
Figure 4B:
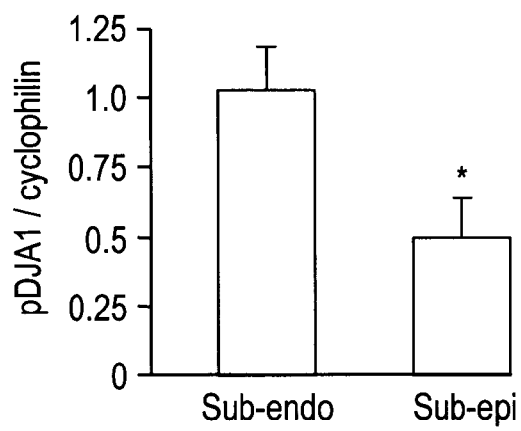
Figure 4C:
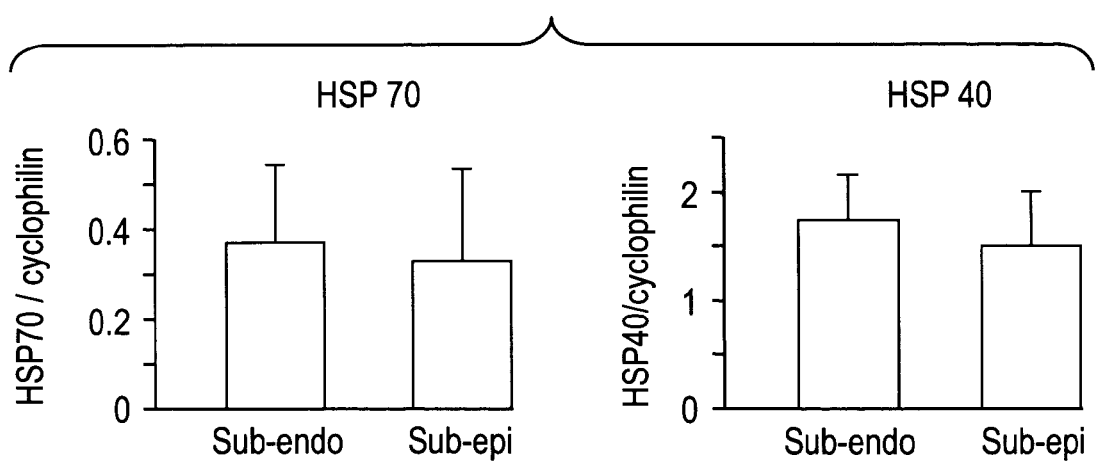

A pig multi-tissue Northern blot was probed, using the original 0.8 Kb fragment of the subtractive hybridization (FIG. 3). This Northern blot showed one specific band at 3.1 Kb, corresponding to the full-length transcript. Remarkably, the expression of pDJA1 was specific for the heart, as it was not detected in the other pig tissues tested, such as stomach, kidney, liver, lung, spleen, aorta or skeletal muscle. The distribution of the pDJA1 transcript in myocardial tissue under baseline conditions was further investigated and compared to the expression of other heat-shock proteins by quantitative PCR (FIG. 4). As shown in FIG. 4A, a higher level of expression of pDJA1 was found in the ventricles when compared to the atria, but the expression in the left ventricle was 2-fold higher than in the right ventricle. Interestingly, a separate analysis of subendocardial and subepicardial samples from the left ventricle showed that the expression of the pDJA1 transcript was double in subendocardium over subepicardium (FIG. 4B). This distribution is specific of pDJA1, because the transcript level of other heat-shock proteins highly expressed in the heart, such as HSP70 and HSP40, did not show any gradient of expression in normal left ventricle (FIG. 4C).

Upregulation of pDJA1 Transcript During Ischemia/Reperfusion

The pDJA1 transcript was found in the subtractive library of stunned myocardium, suggesting that this transcript is upregulated by ischemia. To confirm this, four pig hearts were submitted to 90 minutes coronary stenosis, followed by one hour reperfusion. The expression of pDJA1 in the ischemic area and remote area of the same hearts was measured by Northern blot, and the signal was normalized to the band of the 28S ribosomal RNA. As shown in FIG. 5A, the expression of pDJA1 was increased about 4-fold in the reperfused myocardium.

To further determine the time-course of this increased expression, additional animals were sacrificed at the end of the 90-minute occlusion period, or after 12 hours reperfusion. Sham-operated animals, in which no coronary stenosis was performed, were also included to test the stability of the remote area throughout the protocol. As shown on FIG. 5B, the level of the pDJA1 transcript slightly increased in the subendocardium during the ischemic episode. However, a maximal and transmural increase was observed at 1-hour reperfusion. The difference of expression between subendocardium and subepicardium found in control hearts persisted at all time-points during stunning. At 12 hours reperfusion, the pDJA1 transcript returned to normal values in the ischemic tissue (FIG. 5B). This time-course is similar to that observed for most of the genes which are upregulated in this model of stunning and parallels the progressive functional recovery of stunned myocardium (Depre C., et al., Gene program for cardiac cell survival induced by transient ischemia in conscious pig, *Proc Nat'l Acad Sci U.S.A.* (2001) 98: 9336–9341). The level of the pDJA1 transcript in the remote area was similar to that in sham animals at all time-points. We determined that this increase in pDJA1 expression was myocyte-specific by in-situ hybridization. As shown in FIG. 5C, a strong expression was found in cardiac myocytes from ischemic myocardium, whereas a faint signal was detected in normal myocardium. No signal was detected in endothelial cells.

CYTOPROTECTIVE EFFECT OFpDJA1 IN ISOLATED CARDIAC MYOCYTES

Adenovirus-mediated Transfer of pDJA1

Primary cultures of ventricular cardiac myocytes were prepared from 1-day-old Wistar rats. Cardiac myocytes were dispersed from the ventricles by digestion with 0.1% collagenase type IV (Worthington), 0.1% trypsin (GIBCO) and 15 µg/mL DNase I (Sigma). Cell suspensions were applied on a discontinuous Percoll gradient (1.060/1.082 g/ml) made up in DF buffer containing Dulbecco's Modified Eagle Medium (DMEM)/F12 (1:1, Invitrogen), 17 mM $NaHCO_3$, 2 mM glutamine and 50 µg/ml gentamycin. Cardiac myocytes were plated on culture dishes at a density of $10^6$ cells per well. The culture medium was changed to a serum-free medium after 24 hours.

The coding sequence of pDJA1 was ligated downstream of the CMV promoter in a pDC315 shuttle vector. An adenovirus harboring LacZ was used as a negative control. The recombinant adenoviruses (Ade-pDJA1 and Ade-βGal) were then prepared in 293 cells by cotransfection of a cosmid containing the adenovirus type 5 genome (devoid of E1 and E3) with the shuttle vector, using lipofectamine (GIBCO). Titers were determined on 293 cells overlaid with DMEM plus 5% equine serum and 0.5% agarose. After 24 hours in culture, cardiac myocytes were infected in serum-free medium with the Ade-pDJA1 or the AdeβGal adenovirus. Twenty-four hours after infection, apoptosis was induced by addition of 4 µM staurosporine (Sigma) dissolved in DMSO, and quantified by the activation of caspase-3 (ApoTarget, BioSource).

RESULTS

Cytoprotective Effect of pDJA1 in Isolated Cardiac Myocytes

Figure 6:
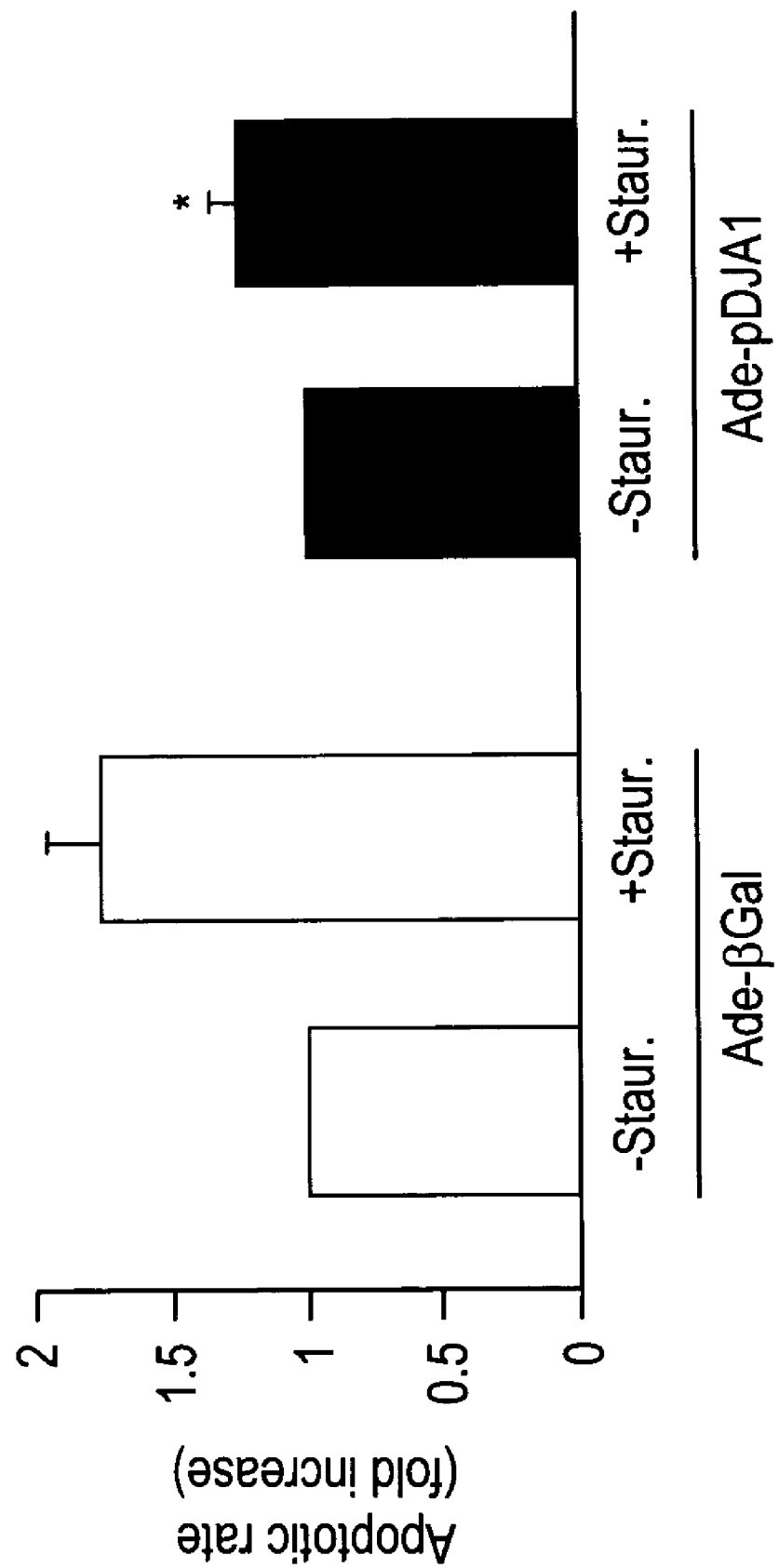
FIG. 6. Cytoprotective effect of pDJA1 in isolated cardiac myocytes. Isolated cardiac myocytes were infected with an adenovirus containing the coding sequence of pDJA1 (Ade-pDJA1), and compared with an adenovirus harboring an irrelevant sequence (Ade-βGal vector). Apoptosis was induced by addition of 4 μM staurosporine for 1 hour and quantified by the measurement of caspase-3 activation (n=3). Values are expressed as the increase in apoptotic rate in both groups after addition of staurosporine (−staur. vs +staur.) *, P<0.05 versus corresponding value in Ade-βGal group.

To confirm that pDJA1 is a co-chaperone participating in cell survival, isolated cardiac myocytes were infected with an adenovirus containing the coding sequence of pDJA1 under the control of the CMV promoter (Ade-pDJA1), and compared with an adenovirus harboring an irrelevant sequence (Ade-βGal vector). Programmed cell death (apoptosis) was induced by addition of 4 µM staurosporine for 1 hour and quantified by the measurement of caspase-3 activation. FIG. 6 shows the increase of apoptotic rate in presence of staurosporine as a percentage of the value found in both groups in absence of staurosporine. After addition of staurosporine, the stimulation of apoptosis in cells transduced with pDJA1 was 65% lower than the values observed in the cells transduced with the control Ade-βGal vector (FIG. 6). Therefore, these data in vitro confirm that overexpression of pDJA1 in myocardium confers a cytoprotective effect.

What is claimed is:

1. An isolated polypeptide encoded by the pDJA1 gene of SEQ ID NO: 1, or a nucleic acid having at least 99% sequence identity with SEQ ID NO: 1, wherein said polypeptide protects against cardiac ischemia.

2. The isolated polypeptide of claim 1, having at least 99% identity with SEQ ID NO: 2.

3. A method of treating cardiovascular disease in a subject in need thereof, comprising administering the polypeptide of claim 1.

4. The method of claim 3, wherein the cardiovascular disease is selected from the group consisting of atherosclerosis, coronary artery disease, ischemic heart disease, myocardial infarction, angina, stroke and other related conditions related to or resulting from an ischemic event.

5. A biomarker associated with and/or predictive of cardiovascular disease, wherein said cardiovascular disease is selected from the group consisting of atherosclerosis, coronary heart disease, ischemic heart disease, myocardial infarction, angina, stroke and other related conditions related to or resulting from an ischemic event, comprising the amino acid sequence of SEQ ID NO:2.

6. A pharmaceutical composition comprising a therapeutically effective amount of a pDJA1 polypeptide encoded by the pDJA1 gene of SEQ ID NO: 1, or a nucleic acid having at least 99% identity to SEQ ID NO: 1, and a pharmaceutically acceptable carrier, wherein said polypeptide protects against cardiac ischemia.

7. A pharmaceutical composition comprising a therapeutically effective amount of a pDJA1 polypeptide comprising an amino acid sequence having at least 99% sequence identity to SEQ ID NO: 2, and a pharmaceutically acceptable carrier, wherein said polypeptide protects against cardiac ischemia.

* * * * *